(12) United States Patent
Noguchi et al.

(10) Patent No.: US 10,408,756 B2
(45) Date of Patent: Sep. 10, 2019

(54) ANALYSIS METHOD AND ANALYSIS APPARATUS

(71) Applicant: FUJITSU LIMITED, Kawasaki-shi, Kanagawa (JP)

(72) Inventors: Michiko Noguchi, Atsugi (JP); Mitsuo Ozaki, Isehara (JP); Yasuhiro Usui, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 287 days.

(21) Appl. No.: 15/417,839

(22) Filed: Jan. 27, 2017

(65) Prior Publication Data

US 2017/0138850 A1 May 18, 2017

Related U.S. Application Data

(63) Continuation of application No. PCT/JP2014/072784, filed on Aug. 29, 2014.

(51) Int. Cl.
*G01N 21/552* (2014.01)
*G01N 21/35* (2014.01)
*G01N 21/65* (2006.01)

(52) U.S. Cl.
CPC ........... *G01N 21/552* (2013.01); *G01N 21/35* (2013.01); *G01N 21/65* (2013.01); *G01N 2021/3595* (2013.01); *G01N 2201/12* (2013.01)

(58) Field of Classification Search
CPC ...... G01N 21/552; G01N 21/35; G01N 21/65; G01N 2201/3595; G01N 2201/12
See application file for complete search history.

(56) References Cited

U.S. PATENT DOCUMENTS

| 3,726,675 | A | * | 4/1973 | Borror | G03C 8/48 |
| | | | | | 252/582 |
| 4,124,592 | A | * | 11/1978 | Bloom | C09B 11/04 |
| | | | | | 430/510 |
| 4,814,254 | A | * | 3/1989 | Naito | G03C 1/49872 |
| | | | | | 219/216 |

(Continued)

FOREIGN PATENT DOCUMENTS

| CN | 102095716 A | 6/2011 |
| EP | 0612996 A2 | 8/1994 |

(Continued)

OTHER PUBLICATIONS

English Translation of JP2012-154718.*

(Continued)

*Primary Examiner* — Marcus H Taningco
*Assistant Examiner* — Djura Malevic
(74) *Attorney, Agent, or Firm* — Kratz, Quintos & Hanson, LLP

(57) ABSTRACT

For an analysis method, a first specimen and a second specimen are prepared, in which different phthalate esters, for example DEHP and DINP, adhere in different states to a pair of predetermined base films, such as PVC, on metal plates. A metal reflection IR spectrum (P) and a metal reflection IR spectrum (Q) are acquired by radiating electromagnetic waves on the prepared first specimen and the second specimen respectively. Significantly different spectra are obtained for different phthalate esters, and the types of phthalate esters are identified by using such spectra.

14 Claims, 24 Drawing Sheets

(56) References Cited

U.S. PATENT DOCUMENTS

| | | | | |
|---|---|---|---|---|
| 5,783,836 | A | * | 7/1998 | Liu ................... G01N 21/552 250/559.4 |
| 5,908,894 | A | * | 6/1999 | Genz ................. B29B 17/0042 521/49 |
| 6,969,736 | B1 | * | 11/2005 | Godwin ................. C08K 5/12 428/379 |
| 7,906,223 | B2 | * | 3/2011 | Rakow ................. C03C 17/38 422/403 |
| 8,871,148 | B2 | * | 10/2014 | Wendland ............. G01N 21/77 356/405 |
| 2003/0035917 | A1 | * | 2/2003 | Hyman ................. B41M 1/30 428/67 |
| 2005/0179548 | A1 | * | 8/2005 | Kittel ............. G06K 19/07798 340/568.2 |
| 2005/0230960 | A1 | * | 10/2005 | Bilodeau ............. G09F 3/0292 283/75 |

FOREIGN PATENT DOCUMENTS

| | | |
|---|---|---|
| EP | 0720014 A1 | 7/1996 |
| JP | 59-155759 A | 9/1984 |
| JP | H08-184560 | 7/1996 |
| JP | 2001-165769 A1 | 6/2001 |
| JP | 2004-53440 A1 | 2/2004 |
| JP | 2012-154718 A1 | 8/2012 |
| JP | 2012-194063 A1 | 10/2012 |
| KR | 10-2013-0066481 A | 6/2013 |
| WO | 94/11126 A1 | 5/1994 |

OTHER PUBLICATIONS

Office Action of Korean Patent Application No. 10-2017-7004762 dated Sep. 18, 2018 (4 pages, 3 pages translation, 7 pages total).

European Patent Application No. 14900392.3: Extended European Search Report dated Jul. 31, 2017.

Rathinam K et al, "The occurrence of 1-14 phthalic acid esters in various samples of commercially available sodium chloride injections (Indian Pharmacopoeia)", Toxicology Letters, Elsevier Biomedical Press, Amsterdam, NL, vol. 15, No. 4, 1983, pp. 329-333.

Xiaoxian et al, "Observing Phthalate Leaching from Plasticized Polymer Films at the Molecular Level", Langmuir vol. 30, No. 17, Apr. 11, 2014, pp. 4933-4944.

International Search Report for International Application No. PCT/JP2014/072784 dated Nov. 25, 2014.

F. Takeuchi, et al.; "Cutting-edge Environmental Technology for Manufacturing Processes;" Fujitsu; 62; 2; Mar. 2014; pp. 54-59 (6 Sheets)/Cited in International Search Report.

European Office Action for corresponding European Application No. 14900392.3 dated Nov. 28, 2017 (7 Sheets).

* cited by examiner

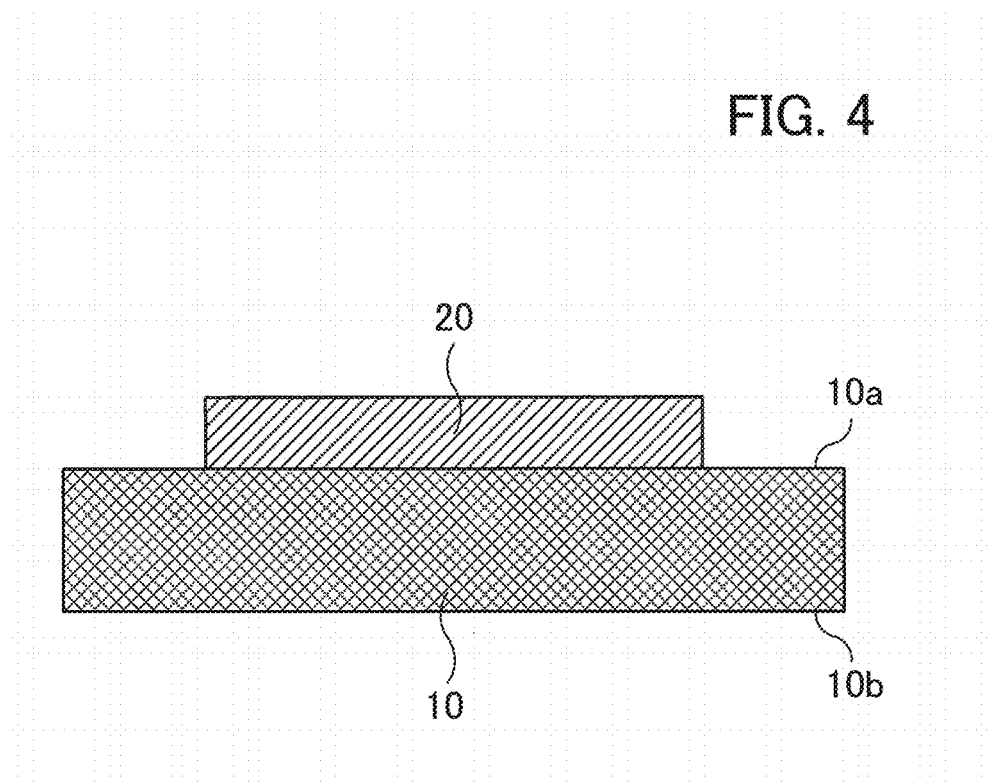

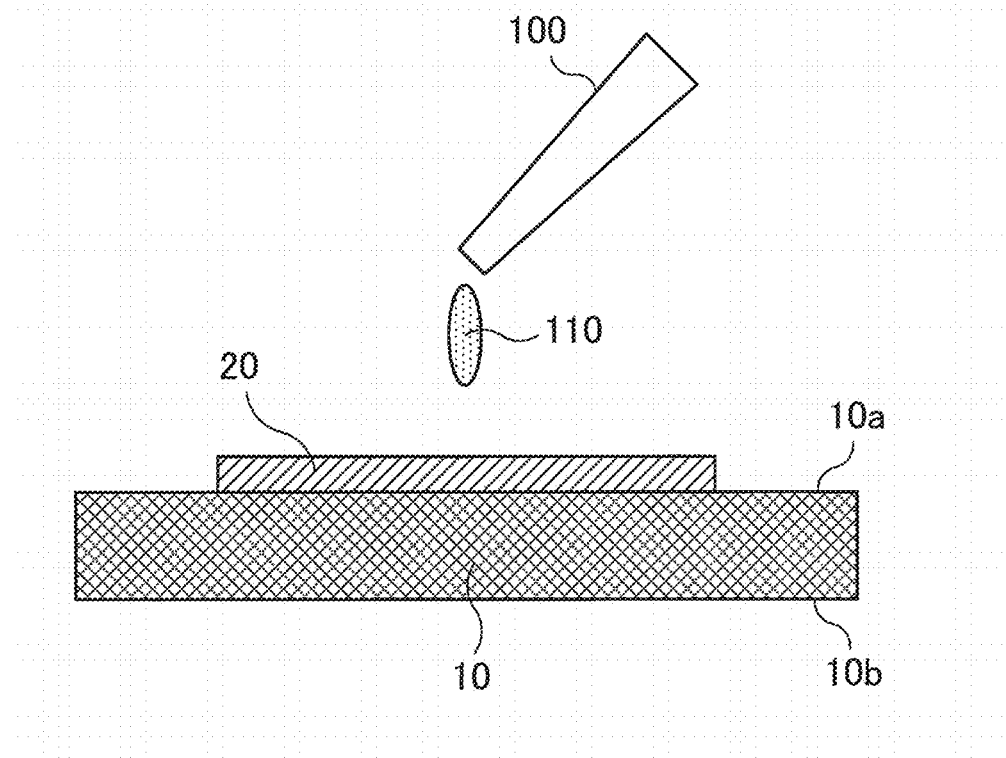

PHTHALATE ESTER ADHERES TO BASE FILM SURFACE (PHTHALATE ESTER IS ORIENTED) ~S10

PHTHALATE ESTER IS ABSORBED IN BASE FILM INNER PORTION (PHTHALATE ESTER IS NON-ORIENTED) ~S11

FIG. 18

500 DETERMINATION CRITERION TABLE

| No. | PEAK POSITION [cm⁻¹] | PEAK LEVEL BEFORE NORMALIZATION | | PEAK LEVEL AFTER NORMALIZATION | | INTERMEDIATE VALUE | DINP SIGN |
|---|---|---|---|---|---|---|---|
| | | DEHP | DINP | DEHP | DINP | | |
| 1 | 2959.10 | 0.7102 | 1.1676 | 1.080974 | 1.777169 | 1.42907 | + |
| 2 | 2929.76 | 0.6802 | 1.0162 | 1.035312 | 1.546728 | 1.29102 | + |
| 3 | 2873.63 | 0.4547 | 0.6392 | 0.692085 | 0.972907 | 0.8325 | + |
| 4 | 2859.725 | 0.4563 | 0.5982 | 0.694521 | 0.910502 | 0.80251 | + |
| 5 | 1732.215 | 0.8517 | 1.3408 | 1.296347 | 2.040791 | 1.66857 | + |
| 6 | 1463.97 | 0.3372 | 0.4995 | 0.513242 | 0.760274 | 0.63676 | + |
| 7 | 1380.011 | 0.20948 | 0.34507 | 0.318843 | 0.525221 | 0.42203 | + |
| 8 | 1288.699 | 0.8084 | 1.1204 | 1.230441 | 1.705327 | 1.46788 | + |
| 9 | 1074.27 | 0.6024 | 0.4558 | 0.916895 | 0.69376 | 0.80533 | − |
| 10 | 945.897 | 0.108346 | 0.03201 | 0.16491 | 0.048721 | 0.10682 | − |

FIG. 19

<PRODUCT A>

600A DETERMINATION TARGET TABLE

| No. | PEAK POSITION [cm⁻¹] | PEAK LEVEL BEFORE NORMALIZATION | PEAK LEVEL AFTER NORMALIZATION | VALUE FROM WHICH INTERMEDIATE VALUE HAS BEEN SUBTRACTED | DETERMINATION TARGET SIGN |
|---|---|---|---|---|---|
| 1 | 2959.10 | 0.778 | 1.184 | −0.245 | − |
| 2 | 2929.76 | 0.743 | 1.131 | −0.160 | − |
| 3 | 2873.63 | 0.491 | 0.747 | −0.085 | − |
| 4 | 2859.725 | 0.497 | 0.757 | −0.046 | − |
| 5 | 1732.215 | 0.852 | 1.296 | −0.372 | − |
| 6 | 1463.97 | 0.362 | 0.551 | −0.085 | − |
| 7 | 1380.011 | 0.237 | 0.361 | −0.061 | − |
| 8 | 1288.699 | 0.862 | 1.312 | −0.156 | − |
| 9 | 1074.27 | 0.559 | 0.850 | 0.045 | + |
| 10 | 945.897 | 0.677 | 1.031 | 0.924 | + |

FIG. 20

<PRODUCT B>

600B DETERMINATION TARGET TABLE

| No. | PEAK POSITION [cm⁻¹] | PEAK LEVEL BEFORE NORMALIZATION | PEAK LEVEL AFTER NORMALIZATION | VALUE FROM WHICH INTERMEDIATE VALUE HAS BEEN SUBTRACTED | DETERMINATION TARGET SIGN |
|---|---|---|---|---|---|
| 1 | 2959.10 | 1.090 | 1.660 | 0.230 | + |
| 2 | 2929.76 | 1.056 | 1.607 | 0.316 | + |
| 3 | 2873.63 | 0.589 | 0.896 | 0.064 | + |
| 4 | 2859.725 | 0.590 | 0.898 | 0.096 | + |
| 5 | 1732.215 | 1.341 | 2.041 | 0.372 | + |
| 6 | 1463.97 | 0.459 | 0.698 | 0.062 | + |
| 7 | 1380.011 | 0.308 | 0.469 | 0.047 | + |
| 8 | 1288.699 | 1.152 | 1.753 | 0.285 | + |
| 9 | 1074.27 | 0.456 | 0.694 | −0.112 | − |
| 10 | 945.897 | 0.033 | 0.051 | −0.056 | − | ns particularly pointed out in the claims.

ANALYSIS METHOD AND ANALYSIS APPARATUS

CROSS-REFERENCE TO RELATED APPLICATION

This application is a continuation application of International Application PCT/JP2014/072784 filed on Aug. 29, 2014 which designated the U.S., the entire contents of which are incorporated herein by reference.

FIELD

The embodiments discussed herein relate to an analysis method and an analysis apparatus.

BACKGROUND

Phthalate esters are used as plasticizers of resin products, such as polyvinyl chloride, which are used as cable covering material for example. The phthalate esters used as plasticizers are, di (2-ethylHexyl) phthalate (DEHP), dibutyl phthalate (DBP), butylbenzyl phthalate (BBP), diisononyl phthalate (DINP), and the like.

Of these phthalate esters, three phthalate esters DEHP, DBP, and BBP are listed as substances of very high concern (SVHC), in the regulation of REACH (registration, evaluation, authorisation and restriction of chemicals) in Europe. Also, these three substances are listed as regulation candidate substances in the directive of RoHS (Restrictions of the certain Hazardous Substances in electrical and electronic equipment) which restricts use of certain hazardous substances in electrical and electronic equipment.

There is a well-known technology that uses a spectrometric analysis method to analyze phthalate esters included in a product, such as cable covering material mentioned above, in a more time-efficient and cost-efficient manner than gas chromatography mass spectrometry and liquid chromatography mass spectrometry. For example, there is a conventional technology in which a specimen that has collected steam generated by heating cable covering material on a substrate is used to measure an IR spectrum of the specimen by Fourier transform-infrared spectroscopy (FT-IR) in order to determine presence or absence of phthalate esters.

See, for example, Japanese Laid-open Patent Publication No. 2012-154718

The conventional spectrometric analysis technology can determine presence or absence of phthalate esters from a measured spectrum. However, there is no significant difference between spectra of different phthalate esters. Hence, it is sometimes difficult to accurately identify the type of a phthalate ester from the measured spectrum, for example whether the phthalate ester is DEHP which is listed as a regulation candidate of the RoHS directive or DINP which is not listed as a regulation candidate.

SUMMARY

According to one aspect, there is provided an analysis method including: preparing a first specimen and a second specimen in which a first phthalate ester and a second phthalate ester adhere respectively to a first base film and a second base film in different states; and acquiring a first spectrum and a second spectrum by radiating electromagnetic waves on the first specimen and the second specimen, respectively.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 is an explanatory diagram of a preparation step of a base film;

FIG. 5 is an explanatory diagram of an adherence step of a phthalate ester by a falling-drop method;

FIG. 18 illustrates an example of a determination criterion table;

FIG. 19 is a first diagram illustrating an example of a determination target table;

FIG. 20 is a second diagram illustrating an example of a determination target table;

DESCRIPTION OF EMBODIMENTS

First, an example of a technology for analyzing a phthalate ester will be described.

One method for detecting a phthalate ester uses an attenuated total reflection (ATR) FT-IR method (hereinafter, referred to as ATR method). For example, a phthalate ester, such as DEHP and DINP, can be used as a plasticizer of polyvinyl chloride in products such as cable covering material that uses polyvinyl chloride. In the ATR method, presence or absence of the phthalate ester in the product can be detected without destroying the product.

As a method for detecting a phthalate ester, there are gas chromatography mass spectrometry and liquid chromatography mass spectrometry, in addition to the ATR method. Constituents are extracted from a product specimen by using a solvent, and the extracted liquid is analyzed by using gas chromatography mass spectrometry or liquid chromatography mass spectrometry.

The analysis method that uses the gas chromatography mass spectrometry or the liquid chromatography mass spectrometry requires a chemical process that uses chemicals, an expensive analysis apparatus, and process facility, and takes a comparatively long time until an analysis result is obtained. Further, comprehension of the analysis result (identification of a phthalate ester) can require an advanced technology. Hence, it is difficult to employ such an analysis method at a production plant that inspects products to determine whether the products are acceptable, for example. Also, a product, such as cable covering material, can include various additives in addition to a plasticizer, and thus if the product is analyzed directly, a phthalate ester can be detected less accurately.

In contrast, the above ATR method can directly analyze a product without destruction and detect a phthalate ester in a short time comparatively easily.

Note that the analysis that uses the ATR method can determine presence or absence of a phthalate ester in a product, but the type of the detected phthalate ester is difficult to determine.

Figure 1:
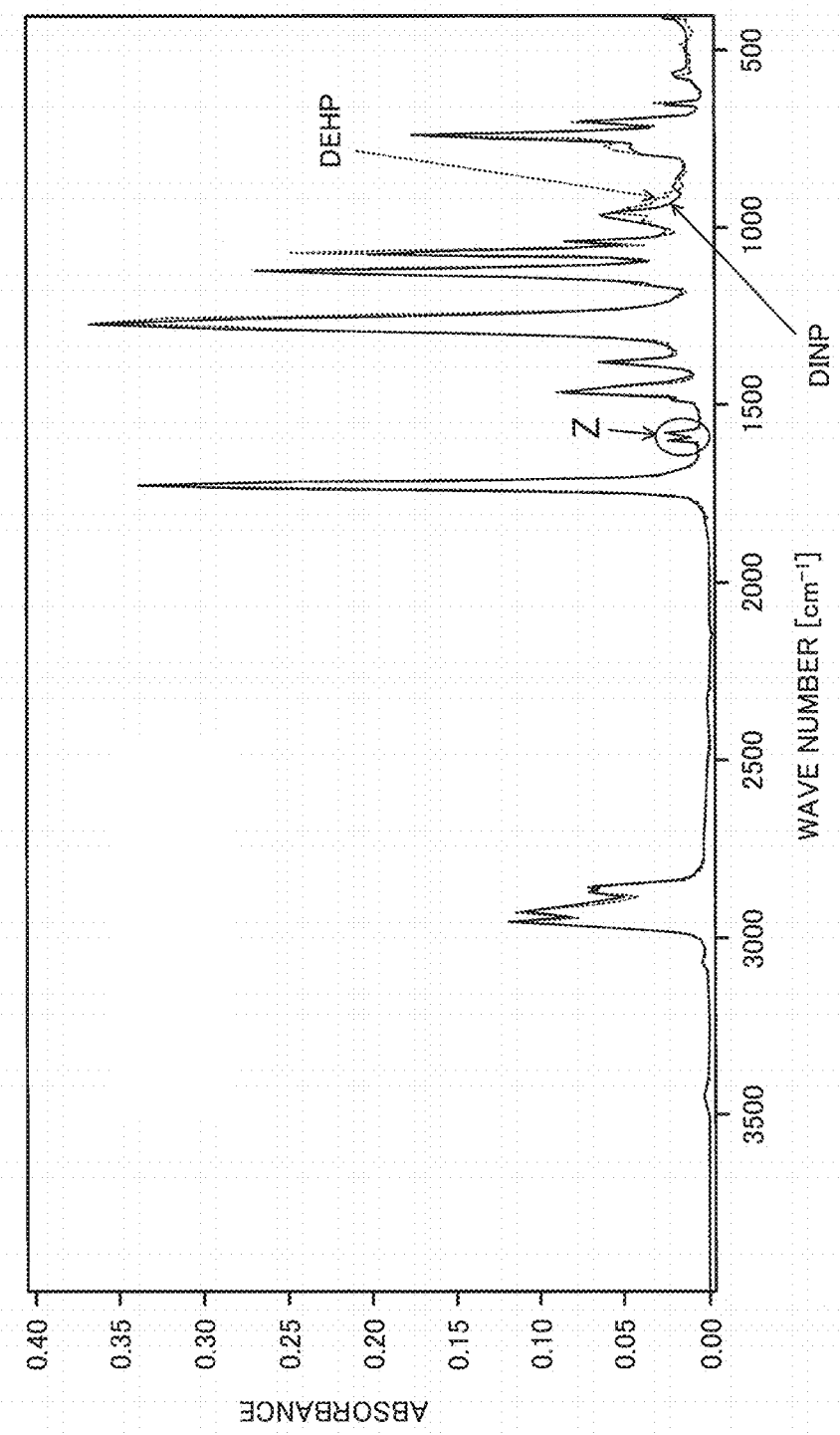
FIG. 1 is a first diagram illustrating an example of ATR-IR spectra of different phthalate esters.

Here, an example of IR spectra acquired by the ATR method (hereinafter, referred to as ATR spectrum or spectra, ATR-IR spectrum or spectra, etc.) of different phthalate esters is illustrated in FIG. 1.

FIG. 1 illustrates ATR spectra of two phthalate esters, including DEHP ($C_{24}H_{38}O_4$) that has a structure of chemical formula (1) and DINP ($C_{26}H_{42}O_4$) that has a structure of chemical formula (2). FIG. 1 illustrates an ATR spectrum of DEHP with a dotted line and an ATR spectrum of DINP with a solid line.

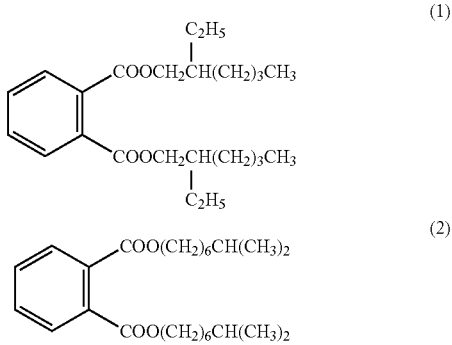

Presence or absence of a phthalate ester can be determined on the basis of the peaks (section Z) at wave numbers 1600 cm$^{-1}$ and 1580 cm$^{-1}$ derived from 1,2-substituted benzene ring, which are characteristic of phthalate esters, in the ATR spectra illustrated in FIG. 1, for example.

However, there is no significant difference between the ATR spectra of DEHP and DINP to distinguish them, as illustrated in FIG. 1. Hence, with the ATR spectra, presence or absence of one or both of DEHP and DINP can be determined, but it is difficult to accurately determine which one of DEHP and DINP is present.

Here, although DEHP and DINP are taken as examples, there is no significant difference between ATR spectra of other different phthalate esters, such as DBP and BBP which are used as plasticizers in the same way. Hence, it is difficult to determine the type of a phthalate ester from an ATR spectrum. Note that chemical formula (3) describes the structure of DBP ($C_{16}H_{22}O_4$), and chemical formula (4) describes the structure of BBP ($C_{19}H_{20}O_4$).

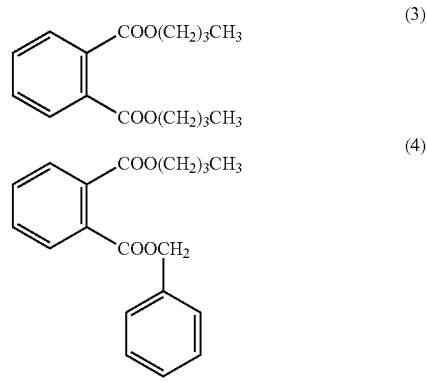

Of phthalate esters including DEHP, DBP, BBP, and DINP, the RoHS directive has listed three phthalate esters DEHP, DBP, and BBP in the regulation candidates and has excluded DINP from the regulation candidates, for example. In the ATR method, whether or not a phthalate ester is detected can be determined on the basis of an ATR spectrum, but it is difficult to determine whether or not the detected phthalate ester is a regulation candidate.

As an FT-IR method, there is a reflection method (hereinafter, referred to as metal reflection method) that obtains an IR spectrum by radiating infrared light at a predetermined angle on a measurement target object on a plate made of metal, such as aluminum, in addition to the above ATR method.

Figure 2:
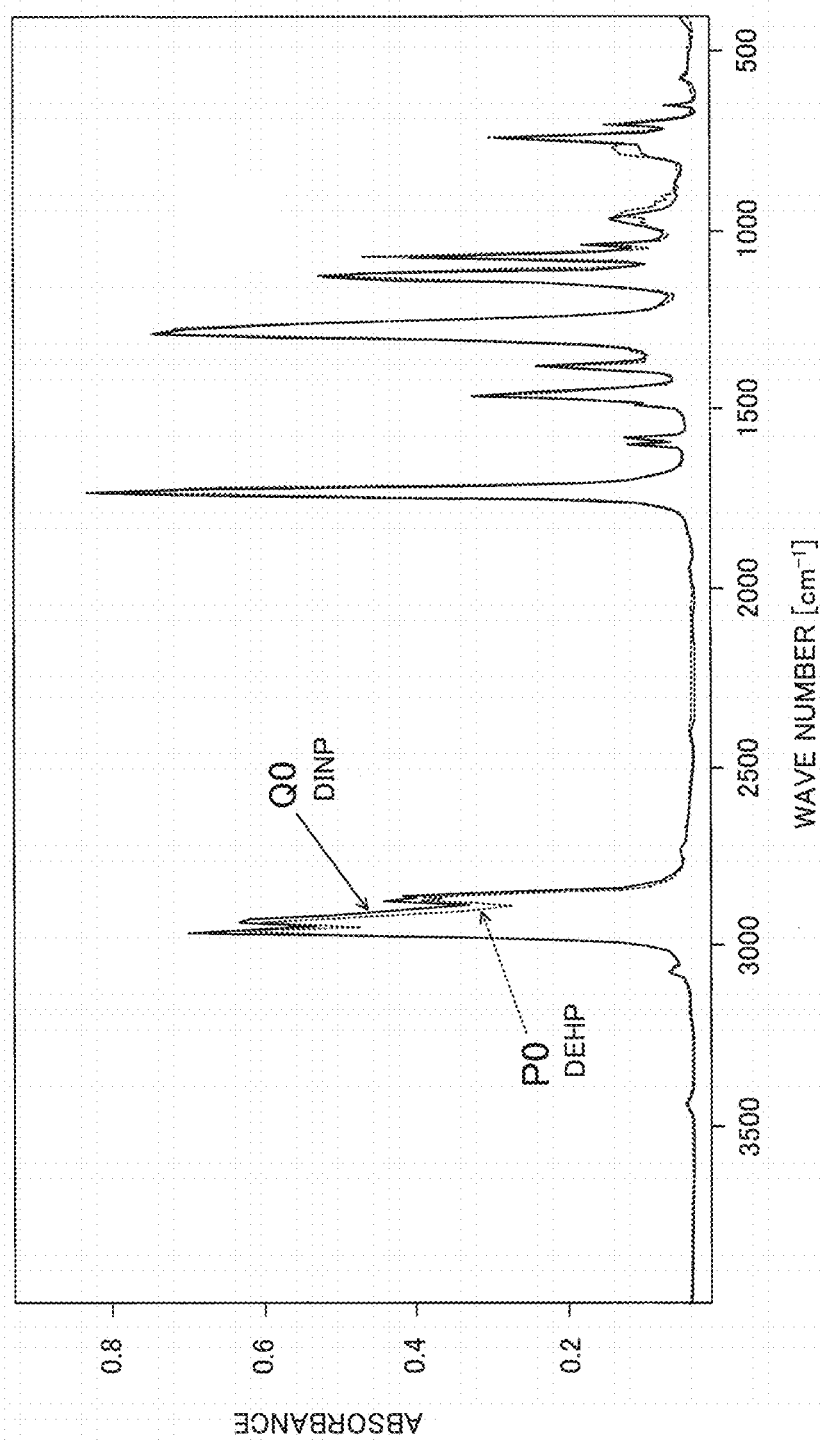
FIG. 2 illustrates an example of metal reflection IR spectra of different phthalate esters.

Here, FIG. 2 illustrates an example of IR spectra (hereinafter, referred to as metal reflection IR spectrum or spectra) of different phthalate esters acquired by the metal reflection method.

FIG. 2 illustrates a metal reflection IR spectrum P0 (a dotted line) of a specimen in which a standard substance of DEHP in the amount of approximately 0.1 mg adheres directly to an aluminum plate, and a metal reflection IR spectrum Q0 (a solid line) of a specimen in which a standard substance of DINP in the amount of approximately 0.1 mg adheres directly to an aluminum plate. The surface reflectances of the aluminum plates in use are 85%. The metal reflection IR spectra P0 and Q0 of the specimens are obtained by radiating infrared light at an incident angle 30° on DEHP and DINP on the aluminum plates.

As illustrated in FIG. 2, there is no significant difference that distinguishes DEHP and DINP, between the metal reflection IR spectra P0 and Q0 of DEHP and DINP that adhere directly to the aluminum plates, in the same way as the above ATR spectrum.

Here, although DEHP and DINP are taken as examples, there is no distinguishable significant difference between metal reflection IR spectra of other different phthalate esters, such as DBP and BBP which adhere to aluminum plates directly. It is difficult to use a metal reflection IR spectrum that is obtained from a specimen in which a phthalate ester directly adheres to an aluminum plate, in determination of the type of the phthalate ester.

In consideration of the above point, a method that can accurately distinguish and determine different phthalate esters by using the FT-IR method will be described in detail in the following.

Figure 3:
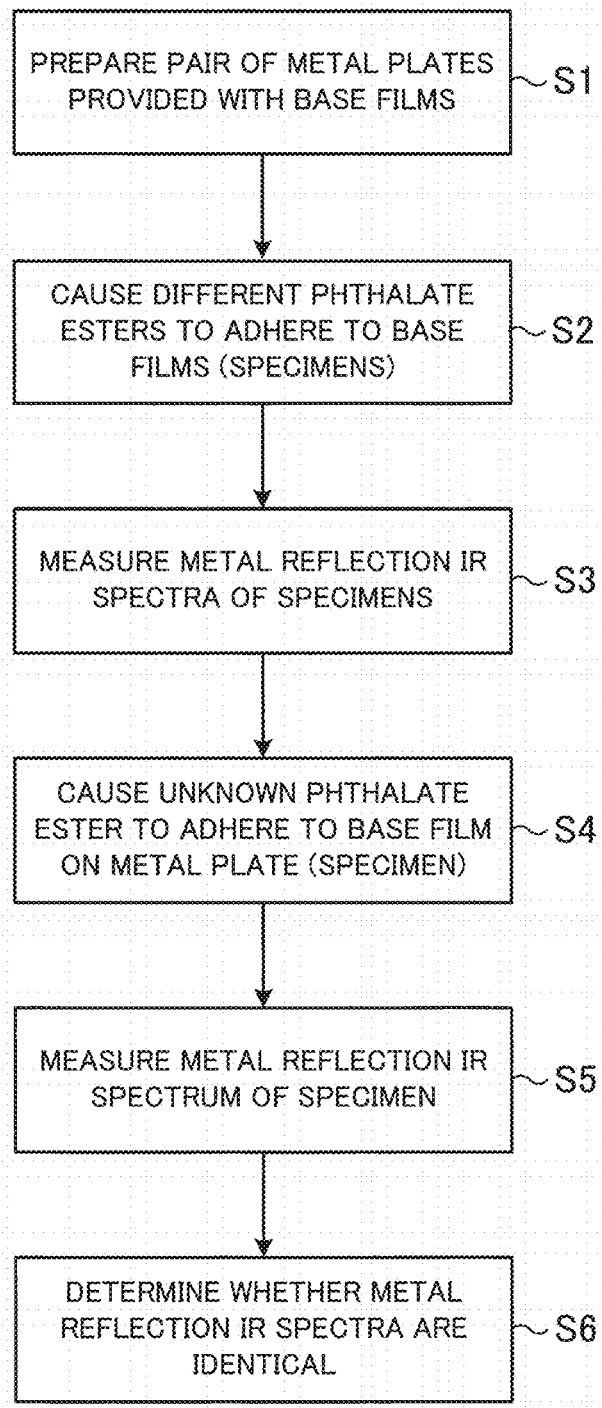
FIG. 3 illustrates an example of an analysis procedure of different phthalate esters.

FIG. 3 illustrates an example of an analysis procedure of different phthalate esters. FIGS. 4 to 7 are explanatory diagrams of steps in the example of the analysis procedure of the different phthalate esters.

The analysis method used here does not allow a phthalate ester to adhere directly to a metal plate as described above, but causes a phthalate ester to adhere to a predetermined base film provided on a metal plate, in order to obtain a metal reflection IR spectrum by the metal reflection method.

FIG. 4 is an explanatory diagram of a preparation step of a base film.

In this analysis method, first, a base film 20 to which a phthalate ester is to adhere is provided on a metal plate 10, as illustrated in FIG. 4 (step S1 of FIG. 3).

The metal plate 10 has a predetermined reflectance (for example, 60% or more) at a surface 10a on which the base film 20 is provided. The metal plate 10 is, for example, an aluminum plate or a stainless plate that has such a predetermined surface reflectance.

A polarized organic film is used as the base film 20. For example, polyvinyl chloride (PVC), polyvinylidene chloride (PVDC), and polyvinyl acetate (PVAc) can be used as the organic film.

A phthalate ester can also be utilized as a plasticizer of PVDC and PVAc in addition to PVC. Materials that can utilize a phthalate ester as a plasticizer can be utilized as the base film 20. Also, a phthalate ester can be utilized as a plasticizer of acrylic resin, polyvinyl butyral, nitrocellulose, urethane, natural rubber, and the like, and these materials can be utilized as the base film 20.

The base film 20 is formed by applying a solution that includes organic material, such as PVC, PVDC, or PVAc, on the metal plate 10 by using a spinner method, for example. Alternatively, the base film 20 may be formed on the metal plate 10 by using a spray method, a dip method, or the like.

The film thickness of the base film 20 provided on the metal plate 10 can be set to 2 μm, for example. Note that the film thickness of the base film 20 is not limited to 2 μm, but can be set within a certain range, such as 0.1 μm to 10 μm, for example. If the base film 20 is too thin, it is possible that a difference is not generated in orientational state between the adhering different phthalate esters as described later, and that a difference is not generated between measured metal reflection IR spectra. Also, if the base film 20 is too thick, it is possible that a preferable metal reflection IR spectrum is not obtained due to light interference that occurs at the time of measurement of the metal reflection IR spectrum. For example, the film thickness of the base film 20 provided on the metal plate 10 is adjusted in consideration of the above point.

A pair of metal plates 10 provided with predetermined base films 20 thereon are prepared as described above, and different phthalate esters whose types are already known are caused to adhere to the respective base films 20 (step S2 of FIG. 3).

Figure 6A:
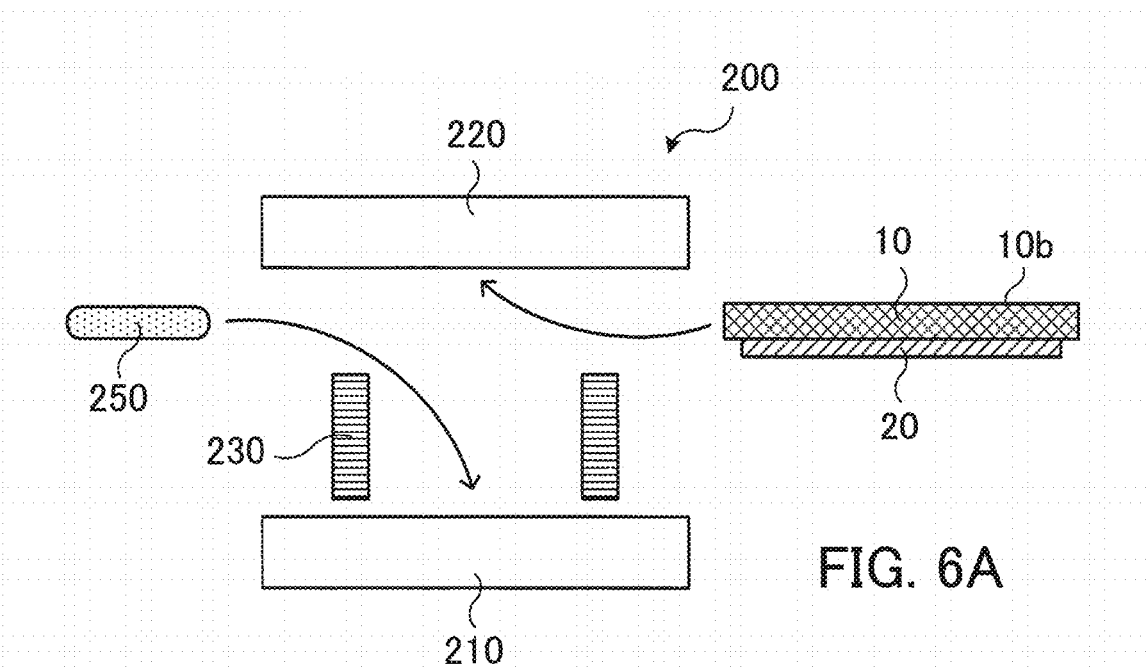
FIGS. 6A to 6C illustrate an explanatory diagram of an adherence step of a phthalate ester by a steam collection method.
Figure 6B:
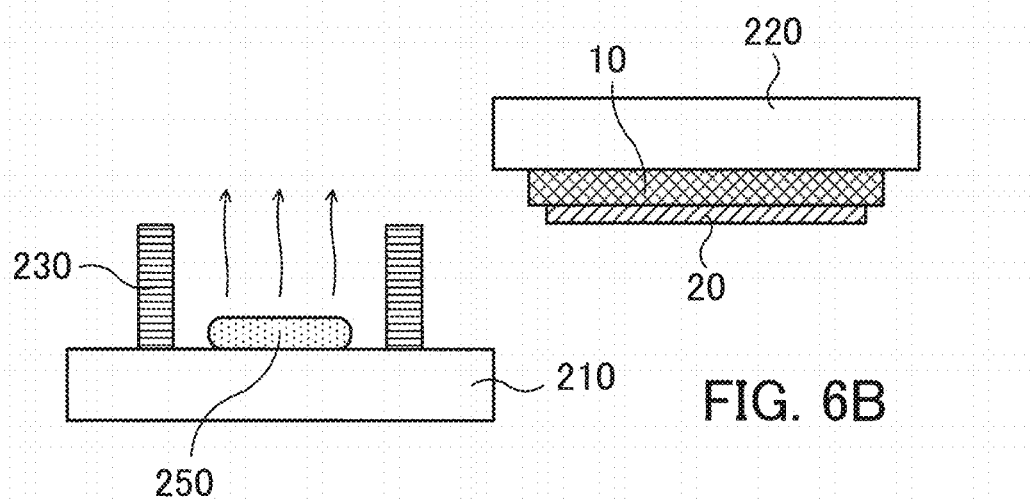
Figure 6C:
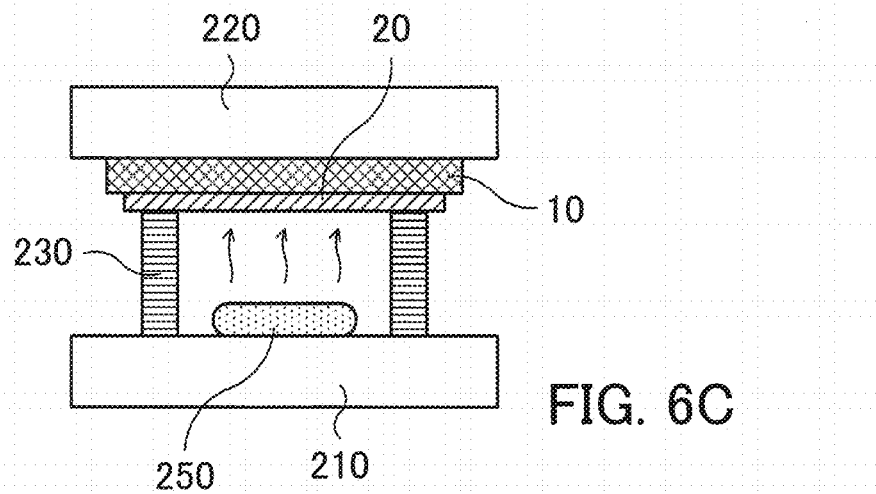

FIGS. 5 and 6A to 6C are explanatory diagrams of an adherence step of a phthalate ester, and FIG. 5 is an explanatory diagram of an adherence step of a phthalate ester by a falling-drop method, and FIGS. 6A to 6C illustrate an explanatory diagram of an adherence step of a phthalate ester by a steam collection method.

For example, a phthalate ester is caused to adhere to the base film 20 by the falling-drop method illustrated in FIG. 5 or the steam collection method illustrated in FIGS. 6A to 6C.

In the falling-drop method, a drop of phthalate ester solution 110 that includes a phthalate ester and a solvent is fallen by using a dropping device 100, such as a dispenser and a pipette, in order to cause the phthalate ester to adhere to the base film 20 on the metal plate 10 as illustrated in FIG. 5. Note that the phthalate ester solution 110 can be prepared by dissolving a predetermined phthalate ester in a predetermined solvent, or can be a commercially available standard product.

For example, different phthalate esters are caused to adhere to the base films 20 provided on a pair of metal plates 10 by the falling-drop method (specimen 360 described later).

Also, in the steam collection method, a phthalate ester is caused to adhere as illustrated in FIGS. 6A to 6C, for example. FIG. 6A is an explanatory diagram of components in a steam collection device, and FIG. 6B is an explanatory diagram of a first process of steam collection by the steam collection device 200, and FIG. 6C is an explanatory diagram of a second process of steam collection by the steam collection device 200.

The steam collection device 200 includes a mounting unit 210, a retention unit 220, and a duct 230, as illustrated in FIG. 6A.

A specimen 250 including a phthalate ester is mounted on the mounting unit 210. The specimen 250 can be a product, such as cable covering material, which includes a phthalate ester, or a solution that includes a phthalate ester. The mounting unit 210 includes a temperature adjusting mechanism that is capable of heating or both of heating and cooling, and adjusts the temperature of the mounted specimen 250 by using the temperature adjusting mechanism.

The retention unit 220 is located to face the mounting unit 210 when collecting steam of the phthalate ester. The retention unit 220 retains the metal plate 10 provided with the base film 20, with a surface retaining the base film 20 facing toward the mounting unit 210. The metal plate 10 is retained by the retention unit 220, by suctioning a back surface 10b which is an opposite side to the surface retaining the base film 20, for example. A temperature adjusting mechanism capable of heating or both of heating and cooling may be provided in the retention unit 220, and the temperature of the base film 20 on the retained metal plate 10 may be adjusted by using the temperature adjusting mechanism.

The duct 230 are provided between the mounting unit 210 and the retention unit 220, when collecting steam of the phthalate ester. The duct 230 is located in such a manner that its duct wall surrounds the specimen 250 mounted on the mounting unit 210, and at the time of steam collection an upper end of the duct 230 that surrounds the specimen 250 as described above is closed by the base film 20 on the metal plate 10 retained by the retention unit 220.

When steam of the phthalate ester is collected, the specimen 250 including the phthalate ester is mounted inside the duct 230 that is provided on the mounting unit 210 as illustrated in FIG. 6B. Also, as illustrated in FIG. 6B, the metal plate 10 provided with the base film 20 is retained by the retention unit 220.

When a product, such as cable covering material, is used as the specimen 250, first, the specimen 250 is heated by using the temperature adjustment mechanism of the mounting unit 210 for a predetermined time (for example, 1 minute) at a predetermined temperature (for example, 180° C.) while the retention unit 220 is brought away from above the mounting unit 210 and the duct 230, for example. This process evaporates additives, such as colorant, that vaporize at a predetermined heating temperature, from the specimen 250 including the phthalate ester. Note that the heating (evaporation) process illustrated in FIG. 6B is needless to be performed, when an additive other than the phthalate ester is not included in the product of the specimen 250, or when the content of an additive does not influence subsequent measurement, for example.

Thereafter, the retention unit 220 that retains the metal plate 10 provided with the base film 20 is moved to upside of the mounting unit 210 and the duct 230, and the upper end of the duct 230 is closed with the base film 20 as illustrated in FIG. 6C.

In this state, the temperature adjustment mechanism of the mounting unit 210 is used to heat the specimen 250 for a predetermined time at a temperature at which the phthalate ester included in the specimen 250 evaporates, in order to cause the steam of the phthalate ester generated from the specimen 250 to adhere to the base film 20 on the metal plate 10. The duct 230 prevents the phthalate ester that evaporates from the specimen 250 from diffusing to the surrounding area, thereby improving collection efficiency onto the base film 20.

For example, the different phthalate esters are caused to adhere to the respective base films 20 provided on a pair of metal plates 10 by the steam collection method (specimens 360 described later).

Metal reflection IR spectra are measured by the metal reflection method, with regard to the specimens in which the different phthalate esters adhere to the base films 20 on the metal plates 10 as described above (step S3 of FIG. 3).

Figure 7:
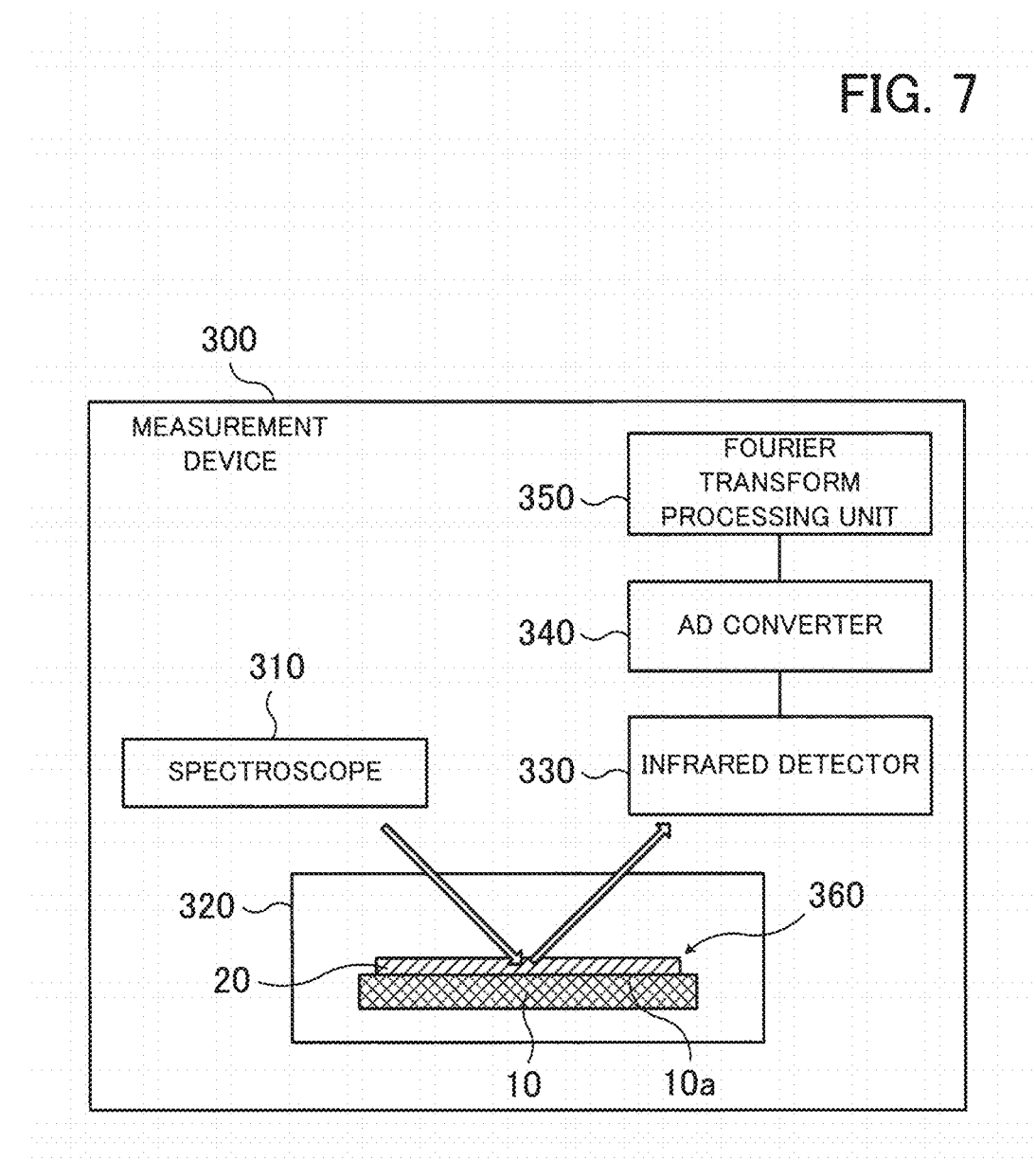
FIG. 7 is an explanatory diagram of a measurement step of a metal reflection IR spectrum.

FIG. 7 is an explanatory diagram of a measurement step of a metal reflection IR spectrum.

The measurement device 300 illustrated in FIG. 7 includes a spectroscope 310, a specimen chamber 320, an infrared detector 330, an AD converter 340, and a Fourier transform processing unit 350.

The spectroscope 310 disperses light, depending on wavelength from an infrared light source, and emits interfering light. In the specimen chamber 320, the aforementioned specimen 360 in which the phthalate ester adheres to the base film 20 on the metal plate 10 is located. The interfering light emitted from the spectroscope 310 is radiated on the base film 20 of the specimen 360 at a certain incident angle (for example, 30°). The interfering light passes through the base film 20, and is reflected at the surface 10a of the metal plate 10, and again is radiated to the outside of the specimen 360 through the base film 20.

The infrared detector 330 detects interfering light that is incident and is radiated to the outside of the specimen 360 as described above. The AD converter 340 digitalizes an analog signal (interferogram) from the infrared detector 330. The Fourier transform processing unit 350 Fourier-transforms the data that is digitalized by the AD converter 340, and generates absorbance in relation to wave number, i.e., a metal reflection IR spectrum.

This measurement device 300 is used to obtain metal reflection IR spectra of specimens 360 in which different phthalate esters adhere to respective base films 20 on metal plates 10.

Figure 8:
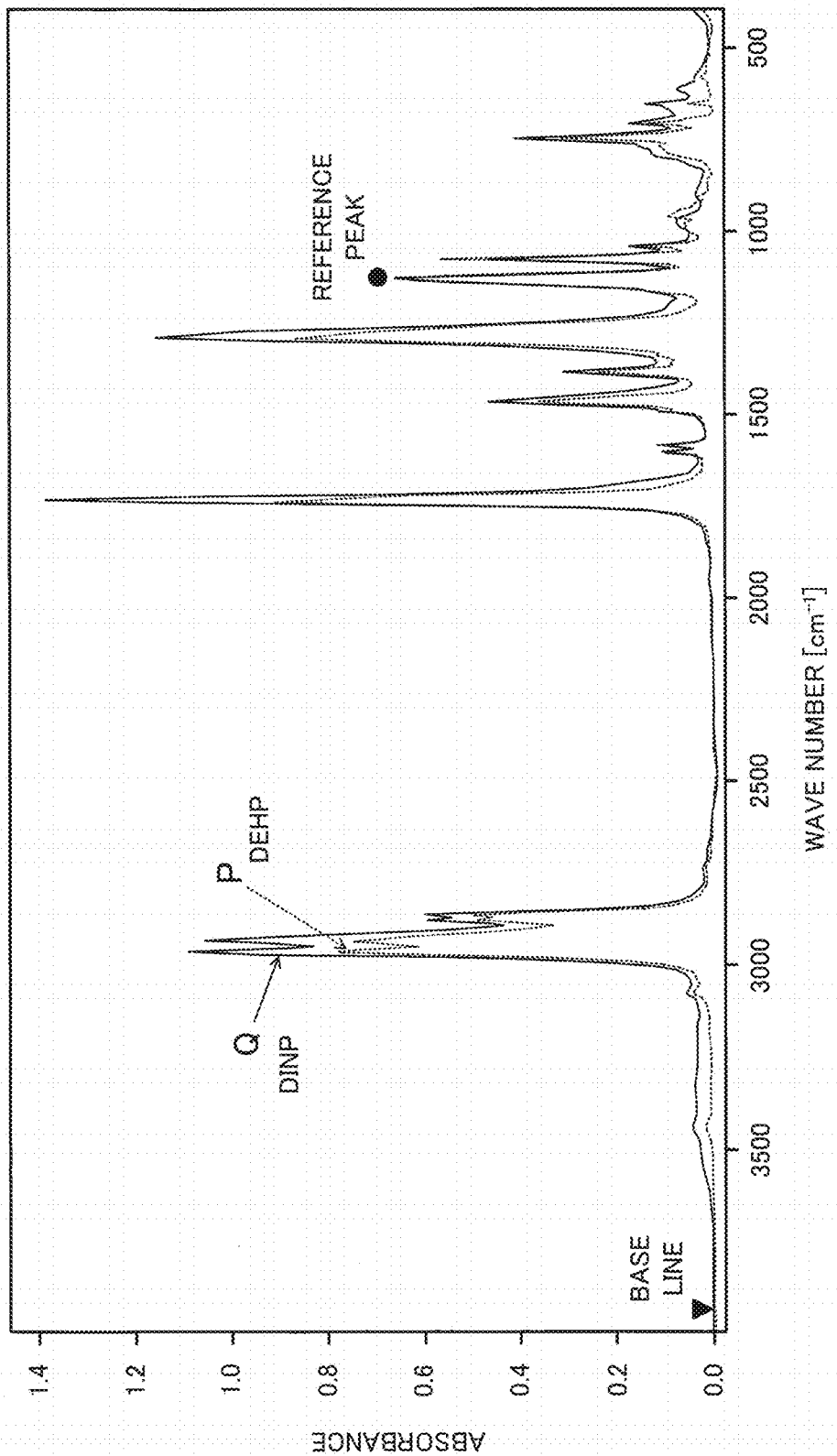
FIG. 8 illustrates an example of metal reflection IR difference spectra (which are generated by subtracting a spectrum of a base film) of specimens in which different phthalate esters adhere to base films.

FIG. 8 illustrates an example of metal reflection IR spectra of specimens in which different phthalate esters adhere to respective base films.

FIG. 8 illustrates a metal reflection IR spectrum (P (dotted line) of FIG. 8) of a specimen 360 in which DEHP adheres to a base film 20 on a metal plate 10, and a metal reflection IR spectrum (Q (solid line) of FIG. 8) of a specimen 360 in which DINP adheres to a base film 20 on a metal plate 10.

Here, aluminum plates of surface reflectance 85% are used as the metal plates 10 of the specimens 360, and PVC films of film thicknesses 2 μm are formed as the base films 20 on the aluminum plates, and standard substances of DEHP and DINP in the amount of approximately 0.1 mg are caused to adhere to the PVC films by the falling-drop method. As described above, the metal reflection IR spectra are obtained by using the measurement device 300 that is configured as described above, with regard to these specimens 360 a certain amount of time (5 minutes) after DEHP and DINP are caused to adhere. The incident angle of the infrared light radiated on the specimens 360 to which DEHP and DINP adhere is set to 30°.

At the time of acquiring the metal reflection IR spectra P and Q of FIG. 8, a blank metal reflection IR spectrum is obtained by radiating infrared light on a specimen (an aluminum plate on which a PVC film is formed with a film thickness of 2 μm) to which DEHP and DINP do not adhere, at an incident angle 30° in the same way. This blank metal reflection IR spectrum is subtracted from the metal reflection IR spectra that are obtained for the specimens 360 to which DEHP and DINP adhere respectively, in order to obtain difference spectra. FIG. 8 illustrates the metal reflection IR spectra P and Q obtained by aligning the base lines of the difference spectra that are measured from two types of specimens 360 as described above. Note that a reference peak illustrated in FIG. 8 will be described later.

As illustrated in FIG. 8, there is a difference between the metal reflection IR spectrum P of the specimen 360 in which DEHP adheres to a PVC film on an aluminum plate and the metal reflection IR spectrum Q of the specimen 360 in which DINP adheres to a PVC film on an aluminum plate. The difference between the metal reflection IR spectra P and Q is not a simple difference between similar figures, but a difference in which levels of absorbance get inverted depending on peak position.

As illustrated in FIG. 2, there is no distinguishable significant difference between the metal reflection IR spectrum P0 of the specimen in which DEHP adheres directly to an aluminum plate and the metal reflection IR spectrum Q0 of the specimen in which DINP adheres directly to an aluminum plate. In contrast, when DEHP and DINP are caused to adhere to the PVC films, the peak positions do not change, but the absorbances (peak levels) at some peak positions change, so that a distinguishable significant difference appears between the metal reflection IR spectra P and Q of DEHP and DINP, as illustrated in FIG. 8.

FIG. 8 illustrates the difference spectra (from which the spectrum of the base film has been subtracted) of metal reflection IR, when DEHP and DINP are used as the different phthalate esters, and PVC films are used as the base films 20. In the same way, a significant difference can be found between IR spectra, when a combination of different phthalate esters, such as DEHP and BBP, DEHP and DBP, and DINP and DBP, adhere to the PVC films.

Figure 9:
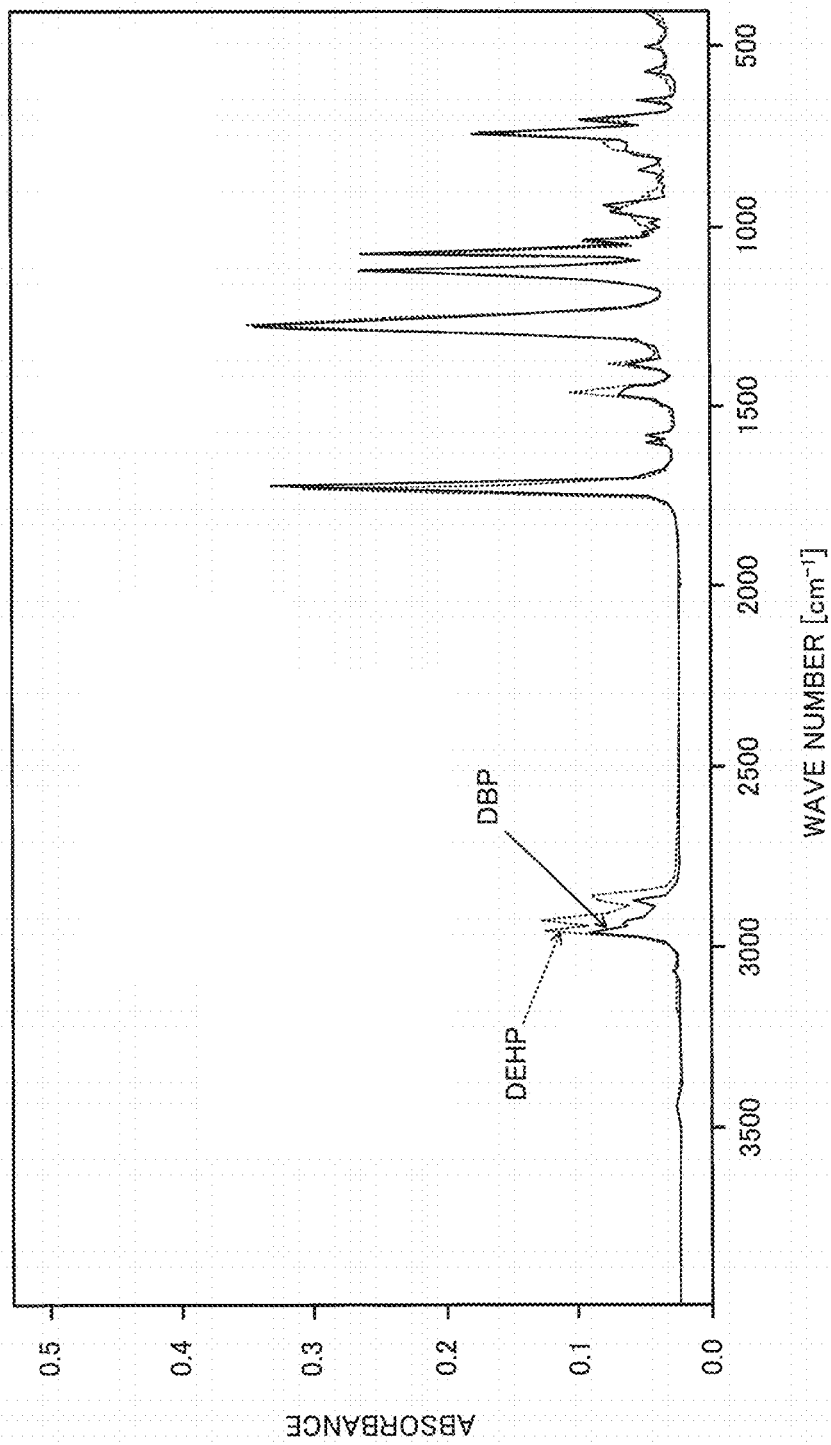
FIG. 9 is a second diagram illustrating an example of ATR-IR spectra of different phthalate esters.
Figure 10:
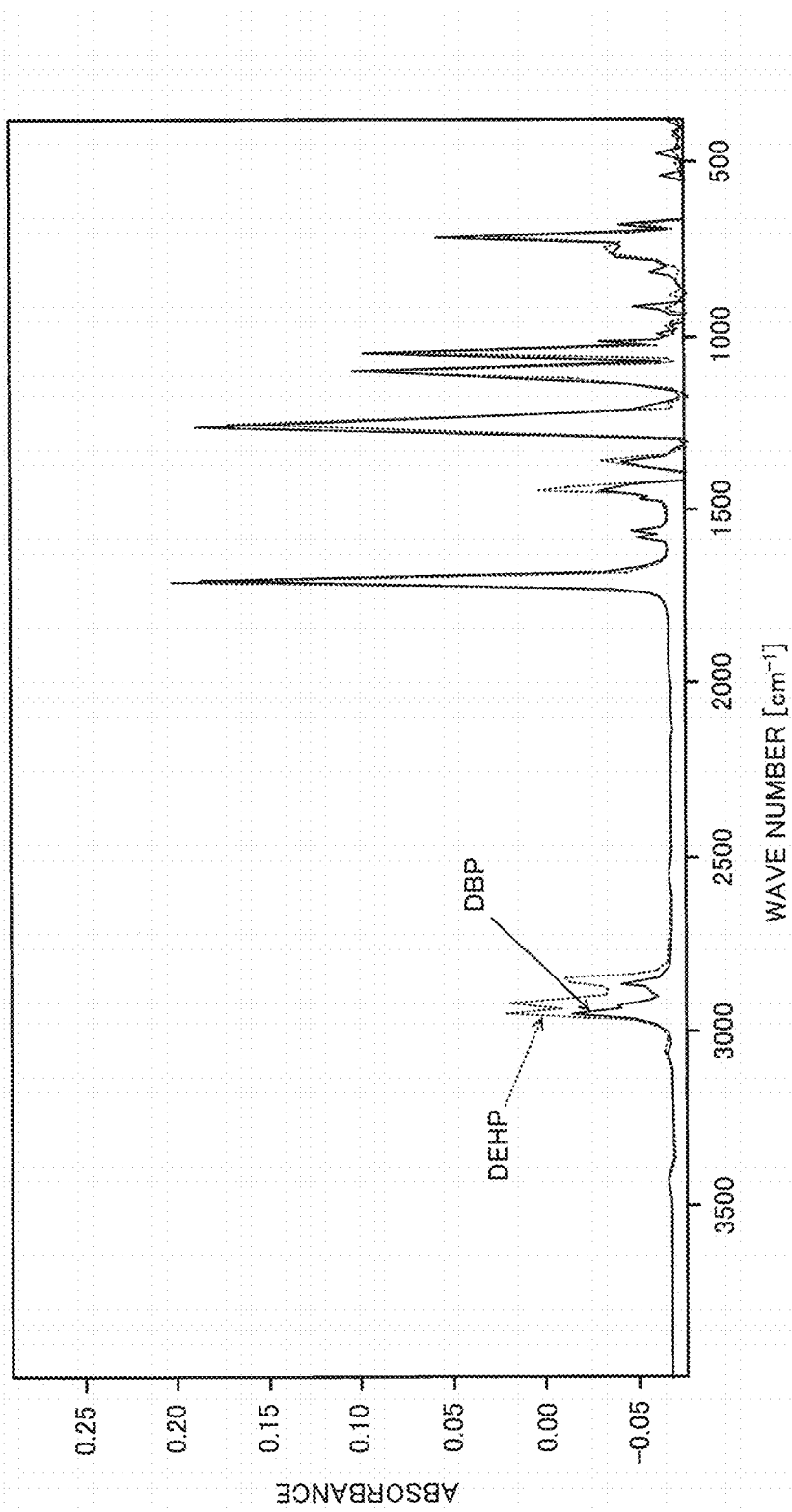
FIG. 10 is a first diagram illustrating an example of ATR-IR difference spectra (which are generated by subtracting a spectrum of a base film) of specimens in which different phthalate esters adhere to base films.
Figure 11:
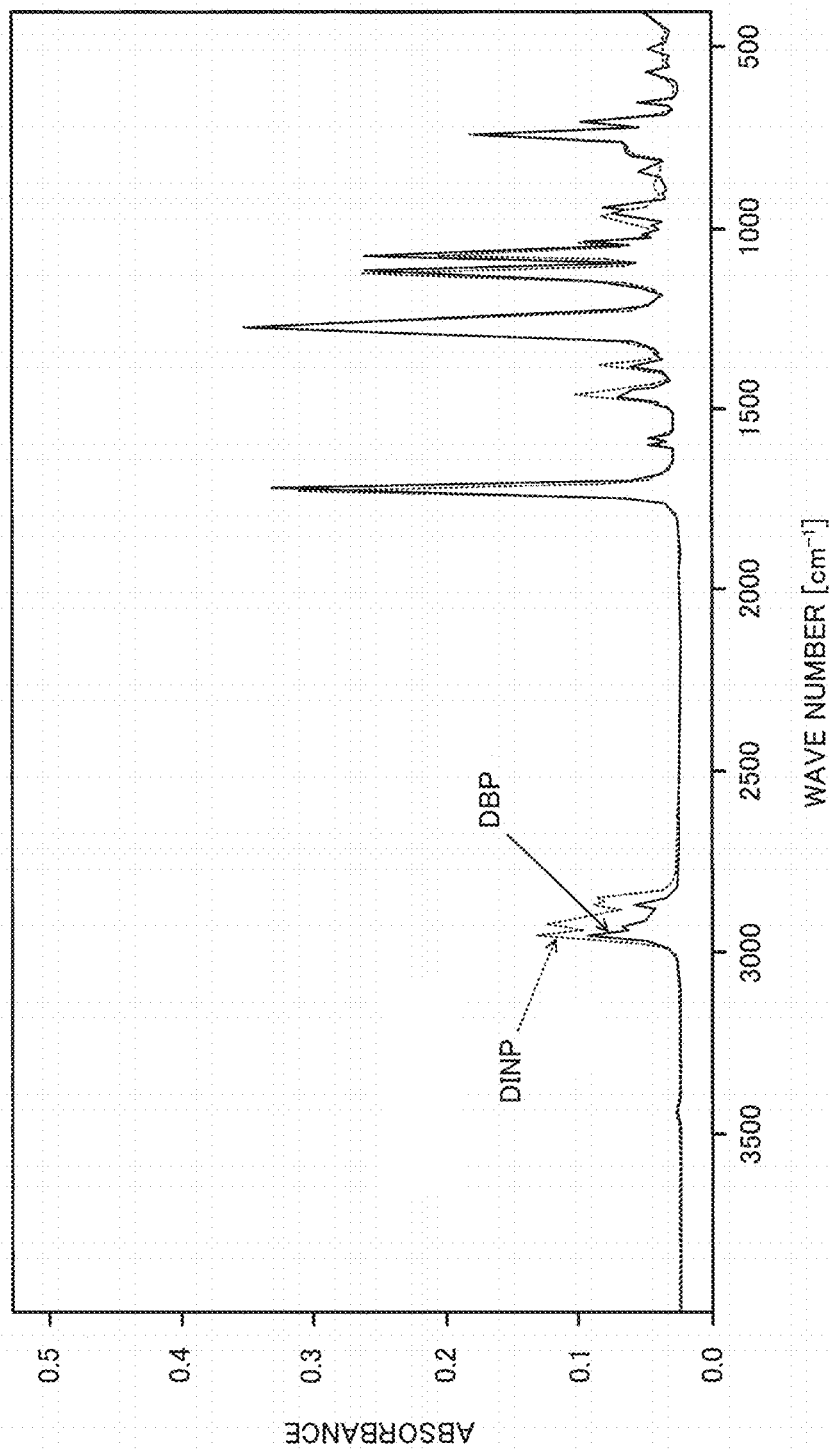
FIG. 11 is a third diagram illustrating another example of ATR-IR spectra of different phthalate esters.
Figure 12:
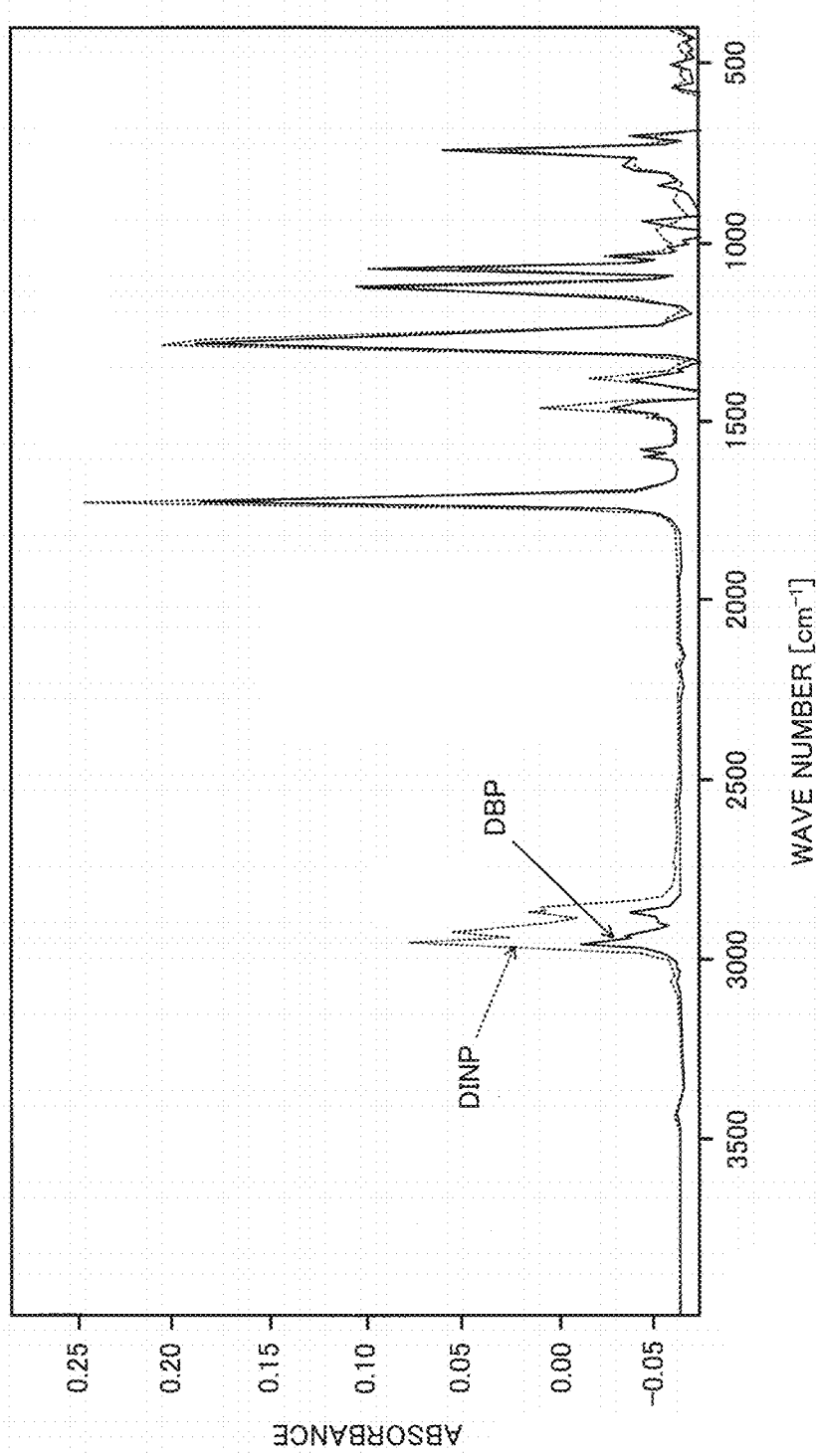
FIG. 12 is a second diagram illustrating an example of ATR-IR difference spectra (which are generated by subtracting a spectrum of a base film) of specimens in which different phthalate esters adhere to base films.

FIGS. 9 to 12 illustrate an example of ATR-IR spectra of different phthalate esters. Here, FIGS. 9 and 10 illustrate examples of IR spectra of DEHP and DBP, and FIGS. 11 and 12 illustrate examples of IR spectra of DINP and DBP.

FIG. 9 is an example of IR spectra of specimens in which DEHP and DBP adhere directly to aluminum plates, and FIG. 10 is an example of ATR-IR difference spectra of specimens in which DEHP and DBP adhere to PVC films on aluminum plates. Also, FIG. 11 is an example of IR spectra of specimens in which DINP and DBP adhere directly to aluminum plates, and FIG. 12 is an example of ATR-IR difference spectra of specimens in which DINP and DBP adhere to PVC films on aluminum plates. Note that FIGS. 10 and 12 illustrate IR spectra from which a blank metal reflection IR spectrum that is obtained for a PVC film on an aluminum plate is subtracted.

FIGS. 9 and 10 indicate that, with regard to DEHP and DBP, a difference between the both IR spectra is more obvious, when DEHP and DBP adhere to the PVC films on the aluminum plates (FIG. 10), than when DEHP and DBP adhere directly to the aluminum plates (FIG. 9). In the same way, FIGS. 11 and 12 indicate that, with regard to DINP and DBP as well, a difference between the both IR spectra is more obvious, when DINP and DBP adhere to the PVC films on the aluminum plates (FIG. 12), than when DINP and DBP adhere directly to the aluminum plates (FIG. 11). As described above, a distinguishable significant difference is generated between the IR spectra of the different phthalate esters, by causing the different phthalate esters to adhere to the PVC films.

A difference is not generated between IR spectra as described above when the different phthalate esters are measured directly, whereas a difference is generated between IR spectra when the different phthalate esters are caused to adhere to predetermined base films, probably for the below reason.

Figure 13:
FIG. 13 is an explanatory diagram of states of phthalate esters that adhere to base films.

Here, FIG. 13 is an explanatory diagram of states of phthalate esters that adhere to base films.

When a phthalate ester adheres to a base film which is an organic film, such as a PVC film, the phthalate ester adheres to a base film surface (step S10), and then is taken (absorbed) into a base film inner portion from the base film surface (step S11). The speed at which the phthalate ester is absorbed into the base film inner portion differs depending on the type of the phthalate ester. Hence, the type of the phthalate ester decides whether a comparatively large amount of phthalate ester remains on the base film surface after the phthalate ester adheres to the base film surface, or a comparatively large amount of phthalate ester is absorbed into the base film inner portion after the phthalate ester adheres to the base film surface.

Meanwhile, it is possible that phthalate ester molecules are not oriented when the phthalate ester molecules exist solitarily or when the phthalate ester molecules are absorbed in the base film inner portion, but are oriented when the phthalate ester molecules adhere to the base film surface. When an IR spectrum is obtained, a difference is generated in peak level due to influence of polarized light, between the non-oriented phthalate ester molecules and the oriented phthalate ester molecules, even at the same peak positions.

Hence, even if the different phthalate esters are measured directly, the phthalate ester molecules are not orientated, and thus it is difficult to obtain a distinguishable IR spectrum including a significant difference. However, although the different phthalate esters in non-orientation state result in IR spectra of the same shape as described above, a difference is generated between the shapes of IR spectra by using the above method that causes the different phthalate esters to adhere to the base films. That is, one of the different phthalate esters is absorbed in the base film inner portion, and the other remains on the base film surface. Thereby, one of the different phthalate esters is not oriented, while the other is oriented, and thus a difference is generated between the shapes of their IR spectra.

Whether the phthalate ester adhering to the base film is absorbed into the base film inner portion or remains on the base film surface is dependent on the types of the phthalate esters and difference in absorption speed into the base films, as described above. For example, one of the different phthalate esters is caused to be absorbed into the base film inner portion, while the other is caused to remain on the base film surface, by utilizing the difference in type and absorption speed.

Figure 22:
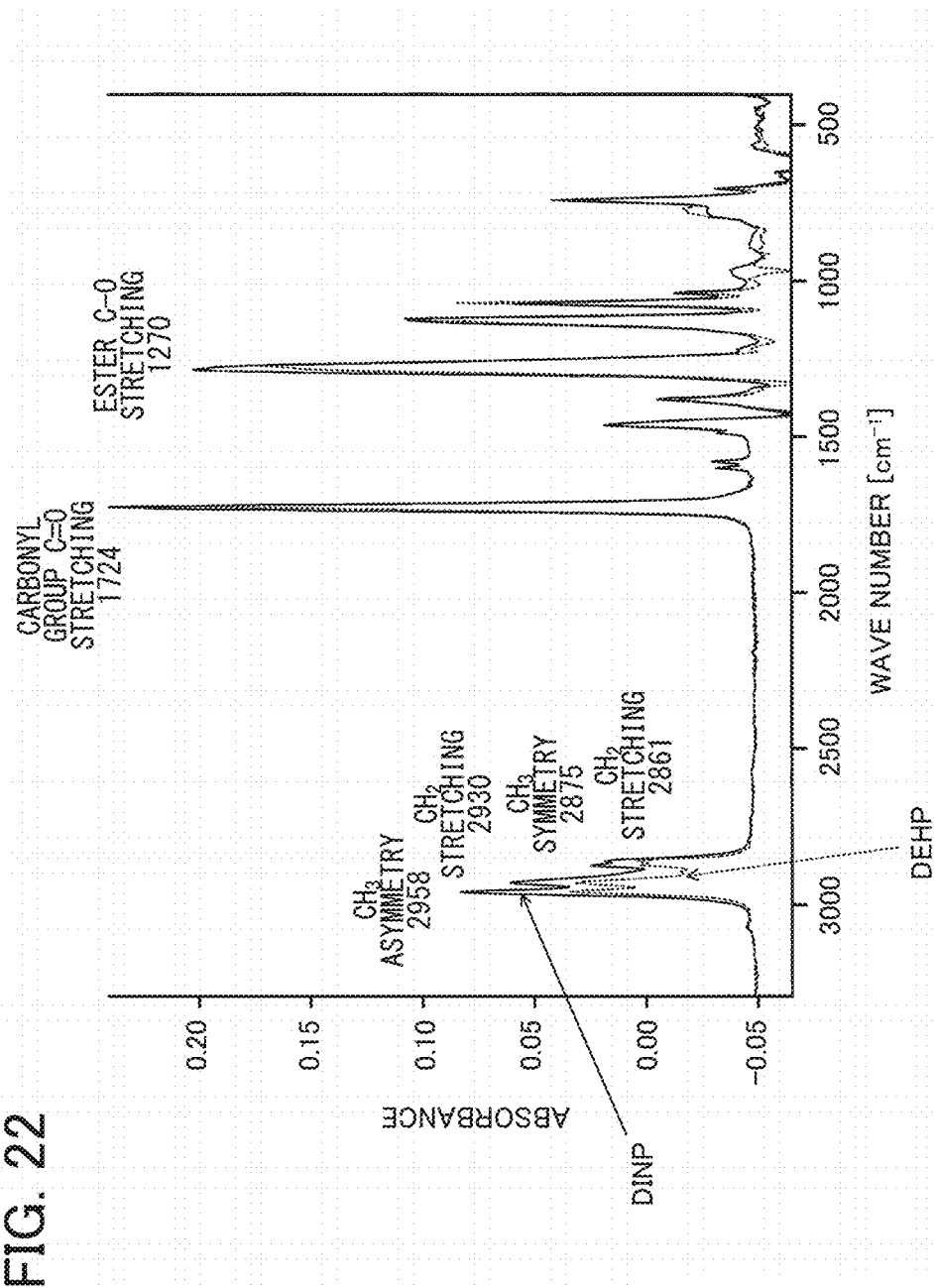
FIG. 22 is a first diagram illustrating an example of an IR spectrum.

In order to obtain this state, the different phthalate esters are caused to adhere to the base films (step S2 of FIG. 3), and thereafter elapse of a certain amount of time is waited to generate a difference between a phthalate ester absorbed into the base film inner portion and another phthalate ester remaining on the base film surface, and thereafter IR spectra are acquired (step S3 of FIG. 3). For example, the IR spectra are acquired 2 hours after the different phthalate esters adhere to the base films. An example of the acquired IR spectra (difference spectra from which the spectrum of the base film has been subtracted) is illustrated in FIG. 22. FIG. 22 illustrates a state in which one (DEHP) of the phthalate esters is absorbed in the base film inner portion, while the other (DINP) remains on the base film surface, 2 hours after the phthalate esters adhere to the base films, resulting in a difference in level.

Figure 23:
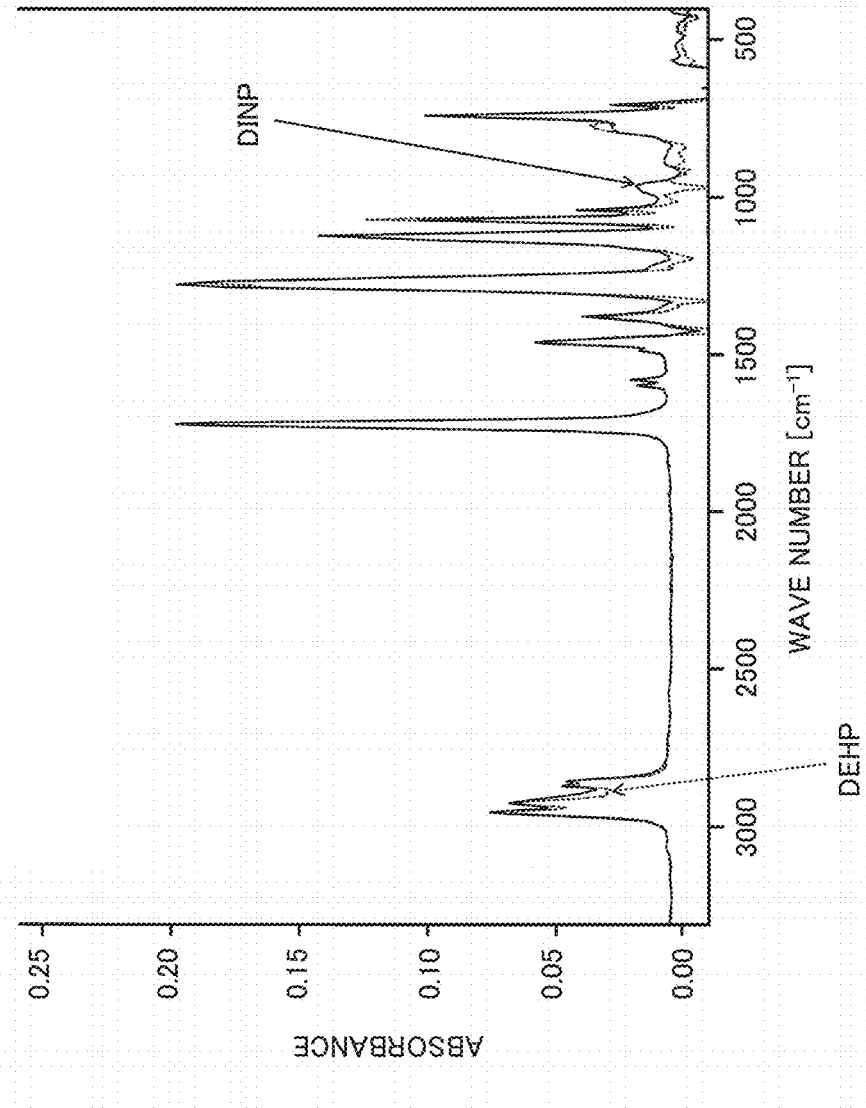
FIG. 23 is a second diagram illustrating an example of an IR spectrum.
Figure 24:
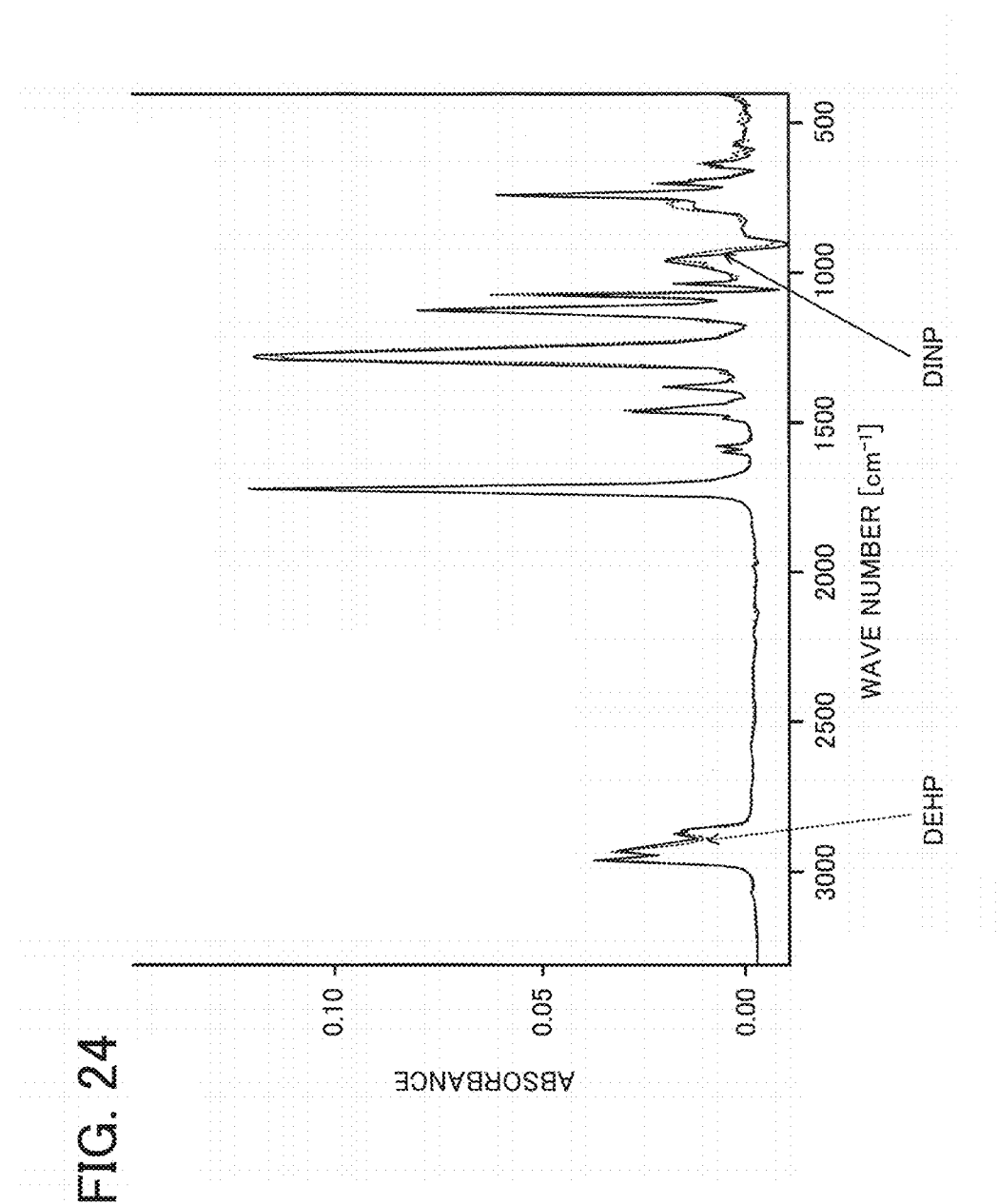
FIG. 24 is a third diagram illustrating an example of an IR spectrum.

FIG. 23 illustrates an example of IR spectra (difference spectra from which the spectrum of the base film has been subtracted) 9 days after adherence to the base films. Also, FIG. 24 illustrates an example of IR spectra (difference spectra from which the spectrum of the base film has been subtracted) of bulk PVC specimens that are produced by adding the phthalate esters to PVC. The IR spectra of FIG. 23 are substantially same as the IR spectra of FIG. 24. FIG. 23 indicates that both of the phthalate esters (DEHP and DINP) are absorbed in the base films, and that the difference between the IR spectra has disappeared.

Note that, when the different phthalate esters become different states, such that one of the different phthalate esters is absorbed into the base film inner portion, while the other remains on the base film surface, immediately after the adherence to the base films, because of the characteristics of the different phthalate esters, it is unnecessary to wait for a certain amount of time to elapse before acquiring the IR spectra.

As described above, the IR spectra of different shapes can be acquired by differentiating the orientational state (orientated, non-orientated) by utilizing the types, and the difference in absorption speed, of the different phthalate esters that adhere to the base films.

Also, the next method can be used to make one of the different phthalate esters to be absorbed in the base film inner portion while the other remains on the base film surface. That is, the present technology can be employed in determination of different phthalate esters in resin.

Specifically, the resin that includes one of the different phthalate esters, for example the resin that includes the phthalate ester that is absorbed into the base film inner portion comparatively easily, is heated to collect the phthalate ester on the base film by the steam collection method. The base film is heated by the temperature adjustment mechanism provided in the retention unit 220 illustrated in FIGS. 6A to 6C. The heating temperature of the base film is set on the basis of the material that is used in the base film. For example, when a PVC film is used as the base film, the use limit temperature of the PVC film is 60° C., and the heatproof temperature of the PVC film is 80° C., and thus the base film is cooled down to a range of 30° C. to 60° C. One of the phthalate esters that has adhered to the base film easily permeates (compatibility) into the base inner portion, when the steam of the phthalate ester is collected on the base film that is heated to a predetermined temperature. In this way, one of the phthalate esters is intentionally caused to be absorbed into the base film inner portion and becomes non-oriented.

Note that, when the steam is collected, the base film is maintained at a higher temperature than an ordinary temperature and in addition is exposed to radiation heat, and thus the phthalate ester is easily absorbed as compared with the falling-drop method. Thus, the time that it takes to generate a difference is shorter than the falling-drop method.

Next, the resin that includes the other of the different phthalate esters, for example the resin that includes the phthalate ester that is not absorbed in the base film inner portion comparatively easily, is heated in the same way in order to cause the phthalate ester to adhere to the base film. Thereby, the other phthalate ester is caused to remain more on the base film surface in an oriented state.

This method is used to differentiate the orientational states (orientated, non-orientated) of the different phthalate esters, in order to acquire metal reflection IR spectra of different shapes.

From the above view point, a base film that causes different phthalate esters to adhere in different orientational states is employed.

Distinguishable IR spectra can be acquired for the different phthalate esters by using predetermined base films.

Also, analysis can be performed to determine the type of an unknown phthalate ester and to determine whether an unknown phthalate ester is identical with a known phthalate ester, by using distinguishable IR spectra of the different phthalate esters. That is, a specimen in which an unknown phthalate ester adheres to a base film on a metal plate is prepared (step S4 of FIG. 3), and a metal reflection IR spectrum of the specimen is measured (step S5 of FIG. 3). Then, it is determined whether the obtained metal reflection IR spectrum is identical with two metal reflection IR spectra that are obtained in the above step S3 (step S6 of FIG. 3).

This analysis method will be described below.

First, an example of an analysis apparatus for use in analysis will be described.

Figure 14:
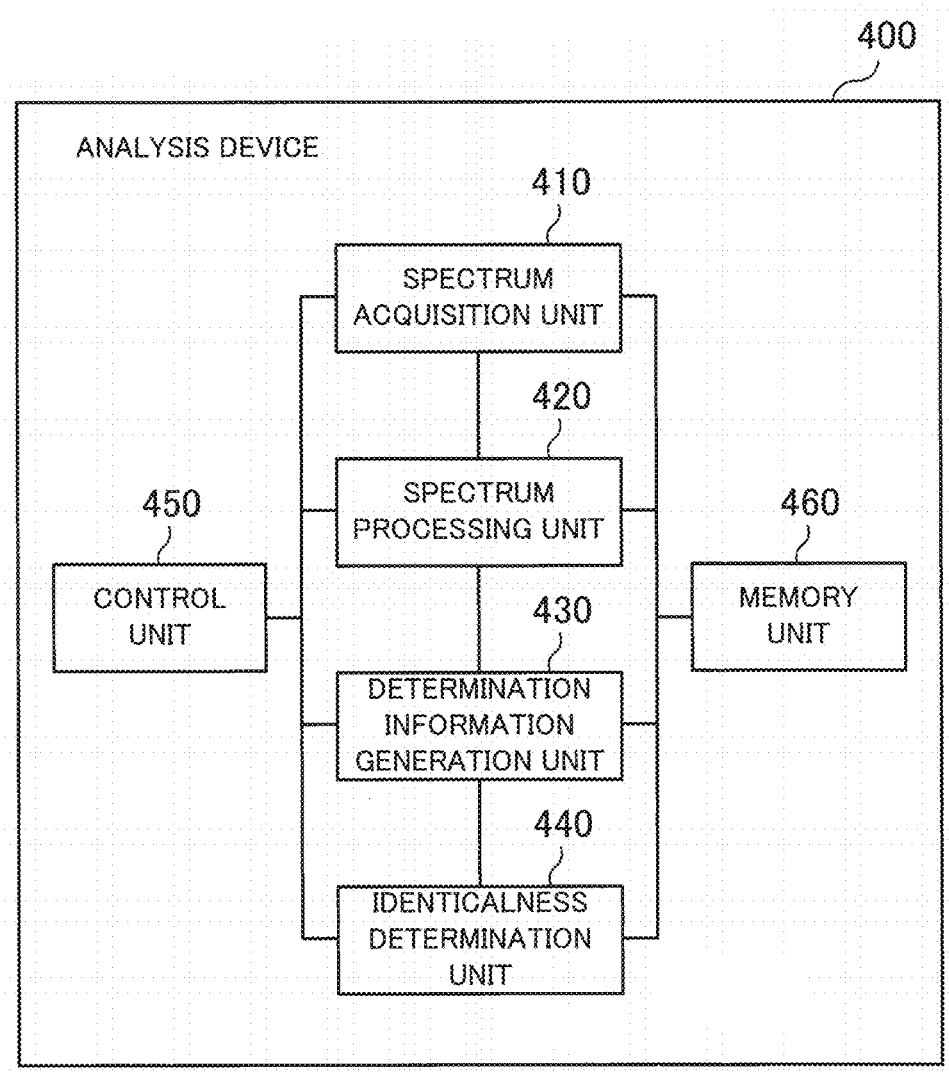
FIG. 14 illustrates an example of an analysis apparatus.

FIG. 14 illustrates an example of the analysis apparatus.

The analysis apparatus 400 illustrated in FIG. 14 includes a spectrum acquisition unit 410, a spectrum processing unit 420, a determination information generation unit 430, and an identicalness determination unit 440. Further, the analysis apparatus 400 illustrated in FIG. 14 includes a control unit 450 and a memory unit 460.

The spectrum acquisition unit 410 acquires a metal reflection IR spectrum of a specimen in which a phthalate ester adheres to a base film on a metal plate.

Here, the spectrum acquisition unit 410 acquires metal reflection IR spectra (a first metal reflection IR spectrum and a second metal reflection IR spectrum) of specimens (a first specimen and a second specimen) in which different known phthalate esters, such as DEHP and DINP, adhere to respective base films on metal plates.

Further, the spectrum acquisition unit 410 acquires a metal reflection IR spectrum (a third metal reflection IR spectrum) of a specimen (a third specimen) in which a phthalate ester (a determination target substance), for which identicalness with those known phthalate esters is to be determined, adheres to a base film on a metal plate.

Also, the spectrum acquisition unit 410 acquires a metal reflection IR spectrum (a blank metal reflection IR spectrum) of a specimen in which a phthalate ester does not adhere to a base film on a metal plate.

The spectrum acquisition unit 410 has a function for measuring the above first to third metal reflection IR spectra and the blank metal reflection IR spectrum, for example. This measurement function is implemented by the measurement device 300 illustrated in FIG. 7, for example. The measurement device 300 is used to measure and acquire the above first to third metal reflection IR spectra and the blank metal reflection IR spectrum.

Alternatively, the spectrum acquisition unit 410 may acquire each metal reflection IR spectrum by receiving data of the above first to third metal reflection IR spectra and the blank metal reflection IR spectrum which are obtained by the measurement device 300 or the like that is used outside the analysis apparatus 400. Also, the spectrum acquisition unit 410 may acquire an ATR-IR spectrum or an IR spectrum by any other method that generates a difference between spectra, instead of the metal reflection IR spectrum.

A specimen provided with a base film on a metal plate is illustrated in FIG. 4, for example. By using such a specimen, the first to third specimens used in measurement of the first to third metal reflection IR spectra are prepared, and the blank metal reflection IR spectrum is measured.

The first specimen that is used in the measurement of the first metal reflection IR spectrum and the second specimen that is used in the measurement of the second metal reflection IR spectrum are prepared by causing known phthalate esters to adhere to the base films on the metal plates by the falling-drop method in FIG. 5 or the steam collection method in FIGS. 6A to 6C. For example, solutions that include the known phthalate esters are caused to adhere to the base films by the falling-drop method, or the phthalate esters in the solutions are caused to adhere to the base films by the steam collection method.

The third specimen that is used in the measurement of the third metal reflection IR spectrum is prepared by causing the phthalate ester of the determination target substance to adhere to the base film on the metal plate, by using the falling-drop method in FIG. 5 or the steam collection method in FIGS. 6A to 6C. For example, solution that includes the phthalate ester of the determination target substance is caused to adhere to the base film by the falling-drop method, or the phthalate ester in the solution or solid is caused to adhere to the base film by the steam collection method. Alternatively, solution or a product such as cable covering material that includes the phthalate ester of the determination target substance is used to cause the phthalate ester to adhere to the base film by the steam collection method.

The spectrum processing unit 420 executes various types of processes that use the first to third metal reflection IR spectra and the blank metal reflection IR spectrum that are acquired by the spectrum acquisition unit 410.

The spectrum processing unit 420 generates difference spectra (first to third difference spectra) between the first to third metal reflection IR spectra and the blank metal reflection IR spectrum that are acquired by the spectrum acquisition unit 410. The spectrum processing unit 420 generates the first to third difference spectra by subtracting the blank metal reflection IR spectrum from the first to third metal reflection IR spectra.

Also, the spectrum processing unit 420 normalizes the generated first to third difference spectra. The spectrum processing unit 420 normalizes the first difference spectrum and the second difference spectrum by using their base lines and levels (absorbances) at a predetermined peak position (reference peak position), and normalizes the third difference spectrum by using its base line and level at the reference peak position. Note that this normalization that uses the base lines and the levels at the reference peak position will be described later.

Further, the spectrum processing unit 420 extracts all or a predetermined part of peak positions that exist in the normalized first to third difference spectra, and levels (peak levels) at the peak positions. The spectrum processing unit 420 extracts peak positions of different levels and peak levels at the peak positions from the normalized first difference spectrum and second difference spectrum, and extracts peak levels at the peak positions from the normalized third difference spectrum.

The determination information generation unit 430 generates various types of information that is used in the determination of whether the phthalate ester of the determination target substance is identical with the known phthalate esters.

For example, the determination information generation unit 430 calculates (generates) intermediate values between the peak levels of both spectra at the peak positions of different levels which are extracted by the spectrum processing unit 420 from the normalized first difference spectrum and second difference spectrum of the known different phthalate esters (for example, DEHP and DINP). Then, the determination information generation unit 430 generates a table (determination criterion table) that includes information indicating, with plus and minus signs, whether peak levels of a spectrum of one of the phthalate esters (for example, DINP) are larger or smaller than the calculated intermediate values.

Also, the determination information generation unit 430 calculates values by subtracting the above intermediate values from the peak levels of the normalized third difference spectrum of the determination target substance at the peak positions that are extracted by the spectrum processing unit 420 from the normalized first difference spectrum and second difference spectrum. Then, the determination information generation unit 430 generates a table (determination target table) that includes plus and minus information of the subtracted values (whether the peak levels are larger or smaller than the intermediate values).

The identicalness determination unit 440 determines whether the determination target substance is identical with the known phthalate esters, by using the information of the determination criterion table and the determination target table that are generated by the determination information generation unit 430.

For example, the identicalness determination unit 440 compares the plus and minus information included in the determination criterion table with the plus and minus information included in the determination target table. Then, the identicalness determination unit 440 determines which one of the known different phthalate esters (for example, DEHP and DINP) is identical with the determination target substance; with what percentage the determination target substance is identical with one of the known different phthalate esters; and whether the determination target substance is not identical with any one of the known different phthalate esters, on the basis of whether or not the plus and minus information are identical with each other.

In the analysis apparatus 400, the control unit 450 controls processing functions of the spectrum acquisition unit 410, the spectrum processing unit 420, the determination information generation unit 430, and the identicalness determination unit 440.

The analysis apparatus 400 includes the memory unit 460 that stores various types of data that are used in processing of the spectrum acquisition unit 410, the spectrum processing unit 420, the determination information generation unit 430, and the identicalness determination unit 440, and various types of data that are obtained in the processing. Also, the analysis apparatus 400 may include an output unit, such as a display device, which outputs such various types of data.

Next, an example of an analysis process flow by the analysis apparatus 400 configured as described above will be described.

Figure 15:
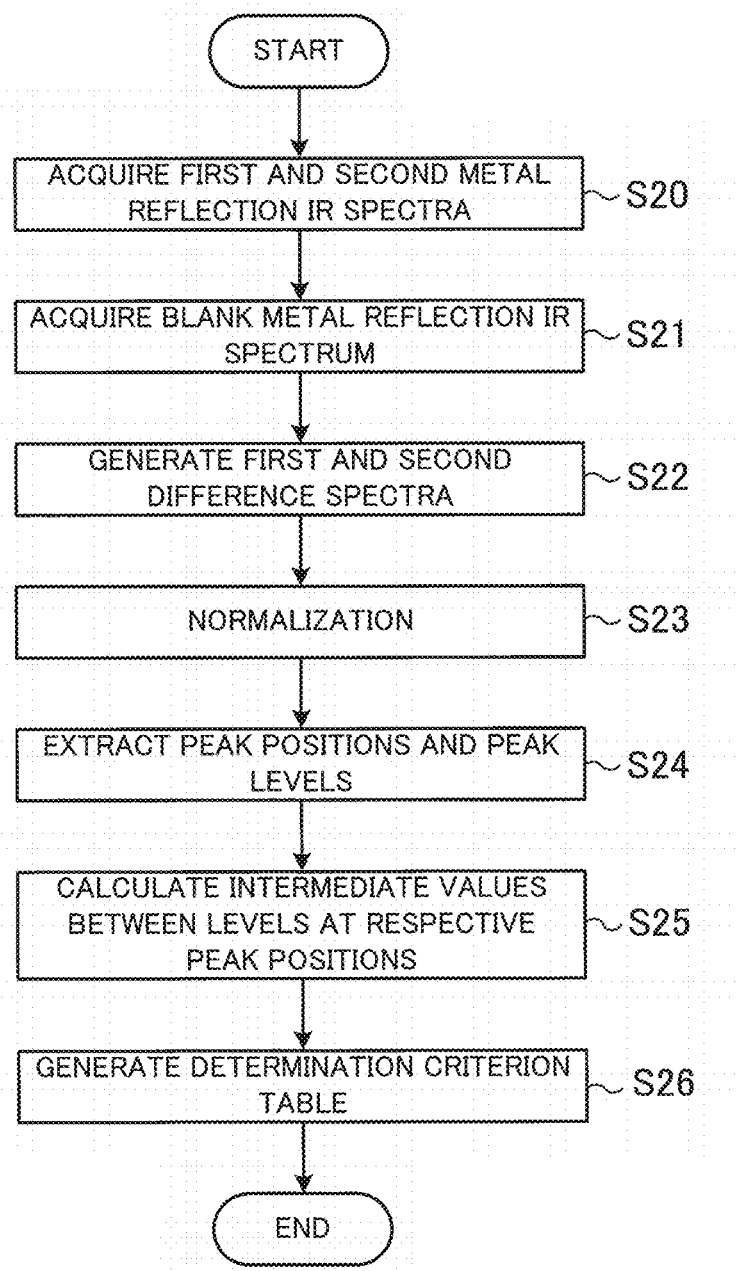
FIG. 15 is a first diagram illustrating an example of an analysis process flow.
Figure 16:
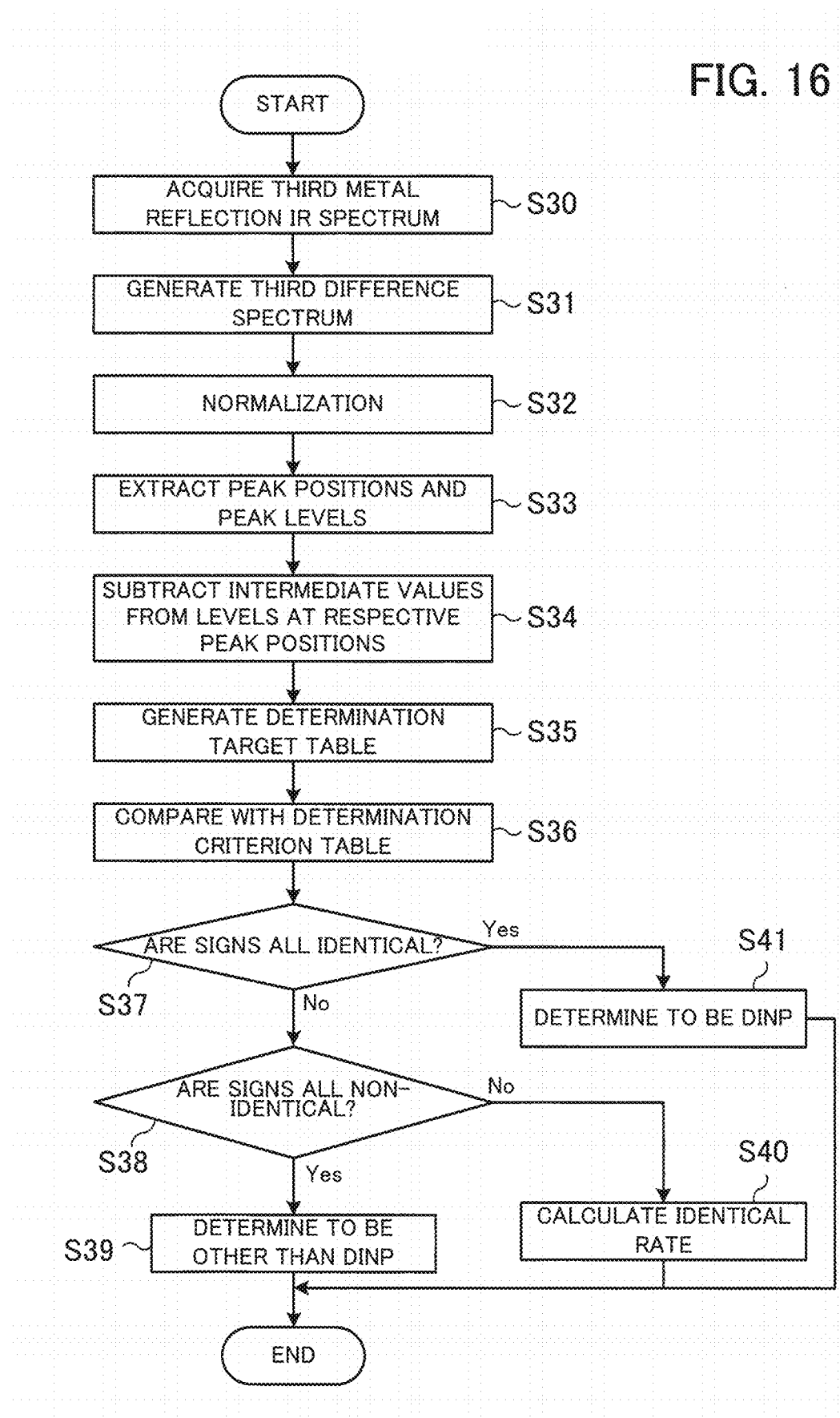
FIG. 16 is a second diagram illustrating an example of an analysis process flow.

FIGS. 15 and 16 illustrate an example of the analysis process flow. FIG. 15 illustrates a process flow for generating a determination criterion, and FIG. 16 illustrates a process flow for determining whether the determination target substance is identical with the known phthalate esters.

First, the analysis apparatus 400 acquires a first metal reflection IR spectrum and a second metal reflection IR spectrum of a first specimen and a second specimen in which known different phthalate esters, for example DEHP and DINP, adhere to base films on metal plates, by means of the spectrum acquisition unit 410 (step S20 of FIG. 15).

Further, the analysis apparatus 400 acquires a blank metal reflection IR spectrum of a specimen in which a phthalate ester does not adhere to a base film on a metal plate, by means of the spectrum acquisition unit 410 (step S21 of FIG. 15).

Thereafter, the analysis apparatus 400 generates a first difference spectrum between the first metal reflection IR spectrum and the blank metal reflection IR spectrum, and generates a second difference spectrum between the second metal reflection IR spectrum and the blank metal reflection IR spectrum, by means of the spectrum processing unit 420 (step S22 of FIG. 15).

For example, the spectra indicated by P and Q of FIG. 8 are acquired as the first difference spectrum and the second difference spectrum, in the processing of steps S20 to S22. A distinguishable significant difference is generated between the first difference spectrum and the second difference spectrum, by causing DEHP and DINP to adhere to predetermined base films on the metal plates.

The analysis apparatus 400 normalizes the generated first difference spectrum and the second difference spectrum by using their base lines and levels at a reference peak position (the position of the reference peak illustrated in FIG. 8), by means of the spectrum processing unit 420 (step S23 of FIG. 15).

This normalization is performed by aligning the base lines of the first difference spectrum and the second difference spectrum and equalizing the levels at the predetermined reference peak position. More specifically, the base lines are aligned, and the entire level of one of the difference spectra is adjusted larger or smaller in such a manner that the level at the reference peak position of one of the first difference spectrum and the second difference spectrum is identical with the level at the reference peak position of the other of the difference spectra.

Figure 17:
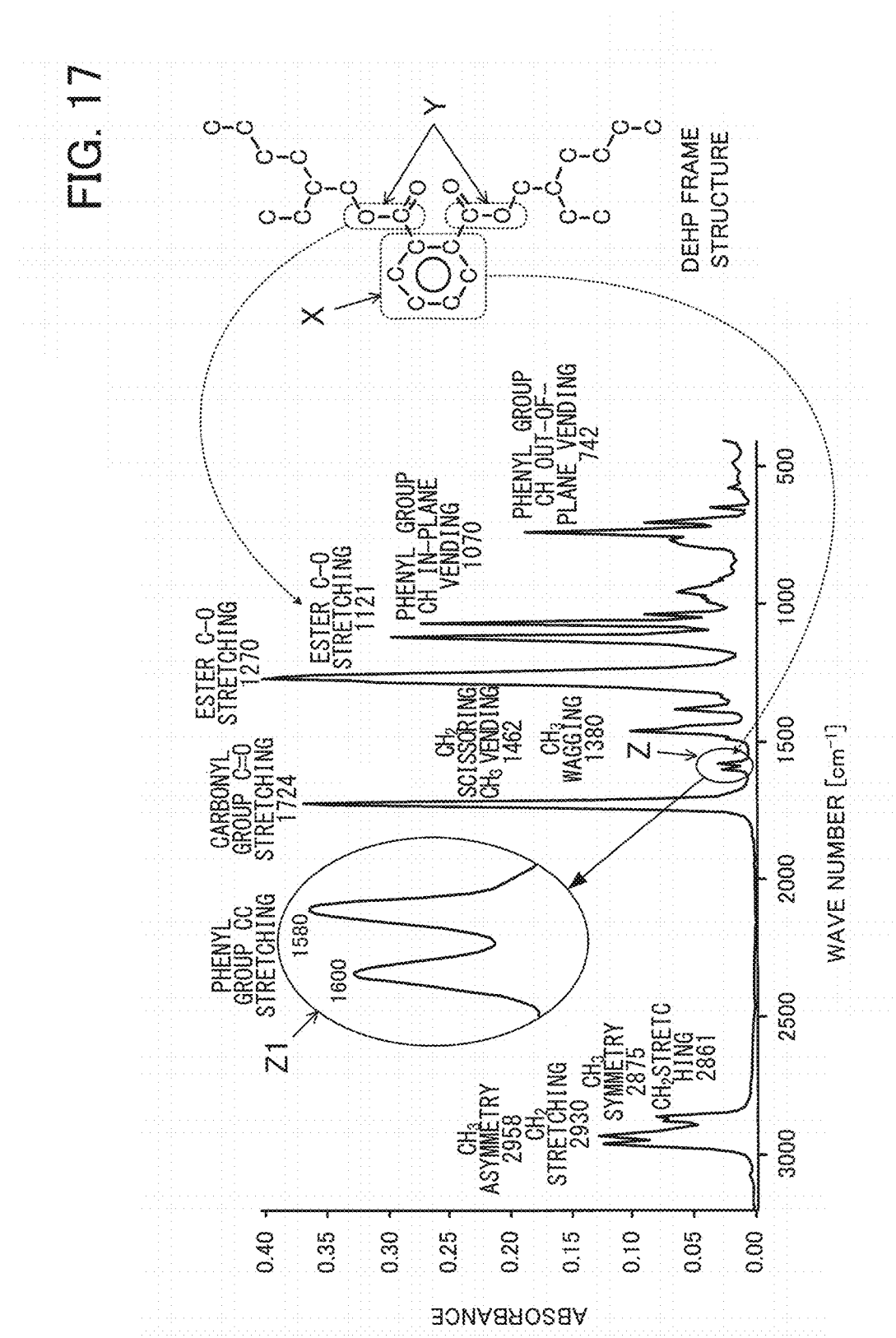
FIG. 17 illustrates peaks and their attributions in an IR spectrum.

For example, a peak position near 1120 cm$^{-1}$ attributed to C—O stretching of esters is employed as the reference peak position that is used in the normalization. This will be described with reference to FIG. 17. FIG. 17 illustrates peaks of an IR spectrum and their attribution.

Presence or absence of a phthalate ester is confirmed from an IR spectrum, by checking the peaks (section Z and section Z1 which is an enlarged view of section Z) at 1600 cm$^{-1}$ and 1580 cm$^{-1}$ derived from 1,2-substituted benzene ring (section X) which are characteristic of phthalate esters. However, their peak levels are small, and thus their errors are too large to use as the reference peak of the normalization which involves the above process of adjusting the levels of the difference spectra. Thus, we searched for a peak of a larger level derived from the structure of phthalate esters which changes its level in proportion to the peaks at 1580 cm$^{-1}$ and 1600 cm$^{-1}$ derived from 1,2-substituted benzene ring. As a result, we found out that a peak near 1120 cm$^{-1}$ attributed to C—O stretching of esters (section Y) is preferable.

On the basis of this knowledge, the peak near 1120 cm$^{-1}$ is employed as the reference peak that is used in the normalization.

After the above normalization, the analysis apparatus 400 extracts peak positions of different levels, and peak levels at the peak positions, from the normalized first difference spectrum and second difference spectrum, by means of the spectrum processing unit 420 (step S24 of FIG. 15).

The peak positions and the peak levels are extracted with regard to at least one peak position. When the peak positions and the peak levels are extracted with regard to a plurality of peak positions, identicalness determination accuracy described later can be improved. Here, an example which extracts a plurality of peak positions of different levels and peak levels at the peak positions will be described.

After a group of peak positions and peak levels are extracted, the analysis apparatus 400 calculates intermediate values between the peak levels of the normalized first difference spectrum and second difference spectrum at respective peak positions, by means of the determination information generation unit 430 (step S25 of FIG. 15).

Then, the analysis apparatus 400 generates a determination criterion table that includes information that indicates, with plus and minus signs, whether the peak levels at respective peak positions of the second difference spectrum of DINP are larger or smaller than the calculated intermediate values, by means of the determination information generation unit 430 (step S26 of FIG. 15).

An example of the determination criterion table is illustrated in FIG. 18.

A determination criterion table 500 of FIG. 18 includes information of ten peak positions (No. 1 to 10) extracted in step S24 and peak levels before and after the normalization of the first difference spectrum (DEHP) and the second difference spectrum (DINP) at the respective peak positions. The determination criterion table 500 further includes information of intermediate values between the peak levels after the normalization of the first difference spectrum (DEHP) and the second difference spectrum (DINP) at the respective peak positions, which are calculated in step S25. The determination criterion table 500 generated in step S26 further includes information (DINP sign) that indicates, with a plus (+) sign, that a peak level of the second difference spectrum (DINP) is larger than a calculated intermediate value and, with a minus (−) sign, that a peak level of the second difference spectrum (DINP) is smaller than a calculated intermediate value, in addition to the above information.

Also, the analysis apparatus 400 acquires a third metal reflection IR spectrum of a third specimen in which a phthalate ester of determination target adheres to a base film on a metal plate, by means of the spectrum acquisition unit 410 (step S30 of FIG. 16).

Thereafter, the analysis apparatus 400 generates a third difference spectrum between the third metal reflection IR spectrum and the blank metal reflection IR spectrum that has been acquired by the spectrum acquisition unit 410 in step S21 previously, by means of the spectrum processing unit 420 (step S31 of FIG. 16). Note that the spectrum acquisition unit 410 may acquire the blank metal reflection IR spectrum again, in order to generate the third difference spectrum.

The analysis apparatus 400 normalizes the generated third difference spectrum by using the base line and the level at the reference peak position, by means of the spectrum processing unit 420 (step S32 of FIG. 16).

This normalization is performed in the same way as the normalization of the first difference spectrum and the second difference spectrum of the above step S23. That is, the base line of the third difference spectrum is aligned to the base lines of the first difference spectrum and the second difference spectrum. Then, the entire level of the third difference spectrum is adjusted larger or smaller, in such a manner that the level at the reference peak position (the peak position that is attributed to C—O stretching near 1120 cm$^{-1}$) of the third difference spectrum is equalized to the levels at the reference peak position of the normalized first difference spectrum and second difference spectrum.

After the normalization, the analysis apparatus 400 extracts predetermined peak positions and peak levels at the peak positions from the normalized third difference spectrum, by means of the spectrum processing unit 420 (step S33 of FIG. 16). From the third difference spectrum, the analysis apparatus 400 extracts a group of peak positions that are extracted because of level difference between the first difference spectrum and the second difference spectrum in the above step S24, and extracts peak levels of the third difference spectrum at the respective peak positions.

Thereafter, the analysis apparatus 400 subtracts the intermediate values that are calculated in the above step S25 from the peak levels of the third difference spectrum at the respective extracted peak positions, by means of the determination information generation unit 430 (step S34 of FIG. 16).

Then, the analysis apparatus 400 generates a determination target table that includes plus and minus information of the values obtained by subtraction, i.e., information indicating whether the peak levels of the third difference spectrum are larger or smaller than the intermediate values, by means of the determination information generation unit 430 (step S35 of FIG. 16).

Examples of determination target tables are illustrated in FIGS. 19 and 20.

Here, two types of cable covering materials (a product A and a product B) including phthalate esters are used as third specimens in order to acquire third metal reflection IR spectra and determination target tables. FIG. 19 illustrates a determination target table 600A that is obtained for the product A, and FIG. 20 illustrates a determination target table 600B that is obtained for the product B.

As for the product A, the third specimen is prepared by causing the phthalate ester included in the product A to adhere to a base film on a metal plate by the steam collection method. Note that, when the third specimen is used to determine whether the phthalate ester is identical with the known phthalate esters, the base film is not heated at a temperature at which the phthalate ester is compatibly dissolved in the inner portion, while the steam of the phthalate ester in the product A is collected. On the contrary, the third specimen is prepared by waiting for a certain amount of time to elapse after the steam is collected, for example.

The third metal reflection IR spectrum is measured from this third specimen. The third metal reflection IR spectrum is acquired by the spectrum acquisition unit 410 (step S30). Then, the third difference spectrum is generated by the spectrum processing unit 420 by using the third metal reflection IR spectrum (step S31), and the third difference spectrum is normalized (step S32), and a group of predetermined peak positions and peak levels at the respective peak positions are extracted (step S33). The intermediate values calculated in the above step S25 are subtracted from the peak levels of the third difference spectrum that are extracted as described above (step S34).

The determination target table 600A of FIG. 19 includes information of extracted ten peak positions (No. 1 to 10), peak levels before and after the normalization of the third difference spectrum at the respective peak positions, and values obtained by subtracting the above intermediate values from the peak levels after the normalization. In step S35, the determination target table 600A is generated, which includes plus and minus information (determination target signs) of the values obtained by subtracting the above intermediate values from the peak levels of the third difference spectrum after the normalization, in addition to the above information.

As for the product B as well, the third specimen is prepared by causing the phthalate ester in the product B to adhere to a base film on a metal plate by the steam collection method. Note that, when the third specimen is used to determine whether the phthalate ester is identical with the known phthalate esters, the base film is not heated at a temperature at which the phthalate ester is compatibly dissolved in the inner portion, while the steam of the phthalate ester in the product B is collected. On the contrary, the third specimen is prepared by waiting for a certain amount of time to elapse after the steam is collected, for example.

The third metal reflection IR spectrum is measured for this third specimen. This third metal reflection IR spectrum is acquired by the spectrum acquisition unit 410 (step S30). Then, the third difference spectrum is generated by the spectrum processing unit 420 by using the third metal reflection IR spectrum (step S31), and the third difference spectrum is normalized (step S32), and a group of predetermined peak positions and peak levels at the respective peak positions are extracted (step S33). The intermediate values calculated in the above step S25 are subtracted from the peak levels of the third difference spectrum that are extracted as described above (step S34).

The determination target table 600B of FIG. 20 includes information of extracted ten peak positions (No. 1 to 10), peak levels before and after the normalization of the third difference spectrum at the respective peak positions, and values obtained by subtracting the above intermediate values from the peak levels after the normalization. In step S35, the determination target table 600B is generated, which includes plus and minus information (determination target signs) of the values obtained by subtracting the above intermediate values from the peak levels of the third difference spectrum after the normalization, in addition to the above information.

In order to evaluate adequacy of determination by the present analysis method in terms of whether the determination target substance is identical with the known phthalate esters, a cable covering material that includes DEHP (30.8 wt %) is used as the product A, and a cable covering material that includes DINP (23.2 wt %) is used as the product B.

The analysis apparatus 400 executes the next process, after generating the determination target table 600A and the determination target table 600B.

First, a process executed by the analysis apparatus 400 will be described, taking an example that uses the determination target table 600A obtained for the product A.

In this case, the analysis apparatus 400 refers to the determination target table 600A (FIG. 19) and the determination criterion table 500 (FIG. 18), by means of the identicalness determination unit 440. The analysis apparatus 400 compares the information of the determination target signs (+/−) in the determination target table 600A with the information of the DINP signs (+/−) in the determination criterion table 500, by means of the identicalness determination unit 440 (step S36 of FIG. 16).

Then, the analysis apparatus 400 determines whether or not all of the determination target signs of the determination target table 600A are identical with the DINP signs of the determination criterion table 500, by means of the identicalness determination unit 440 (step S37 of FIG. 16).

In this example, the determination target signs (+/−) at the respective peak positions (No. 1 to 10) of the determination target table 600A are completely contrary to the DINP signs (+/−) at the respective peak positions (No. 1 to 10) of the determination criterion table 500.

When the determination target signs and the DINP signs are all non-identical with each other as in this example, the analysis apparatus 400 determines whether or not the determination target signs and the DINP signs are all non-identical, by means of the identicalness determination unit 440, (step S38 of FIG. 16). Then, if all are non-identical as in this example, the analysis apparatus 400 determines that the phthalate ester of the determination target substance included in the product A for which this determination target table 600A is obtained is other than DINP (DEHP in this example), by means of the identicalness determination unit 440 (step S39 of FIG. 16).

If not all of but a part of the determination target signs are identical with the DINP signs (step S38 of FIG. 16), an identical rate (=[the number of identical peak positions]/[the number of all peak positions]) is calculated (step S40 of FIG. 16). Identicalness and an identicalness probability of the determination target substance in relation to DINP can be evaluated by using this identical rate.

Next, a process executed by the analysis apparatus 400 will be described, taking an example that uses the determination target table 600B obtained for the product B.

In this case, the analysis apparatus 400 compares the determination target signs and the DINP signs with each other, with reference to the determination target table 600B (FIG. 20) and the determination criterion table 500 (FIG. 18), by means of the identicalness determination unit 440 (step S36 of FIG. 16).

Then, the analysis apparatus 400 determines whether or not all of the determination target signs of the determination target table 600B are identical with the DINP signs of the determination criterion table 500, by means of the identicalness determination unit 440 (step S37 of FIG. 16).

In this example, all of the determination target signs (+/−) at the respective peak positions (No. 1 to 10) of the determination target table 600B are identical with the DINP signs (+/−) at the respective peak positions (No. 1 to 10) of the determination criterion table 500.

When all of the determination target signs are identical with the DINP signs as in this example, the analysis apparatus 400 determines that the phthalate ester of the determination target substance included in the product B for which this determination target table 600B is obtained is DINP, by means of the identicalness determination unit 440 (step S41 of FIG. 16).

The above process by the analysis apparatus 400 can evaluate whether the phthalate ester of the determination target substance included in the product is DINP or other than DINP, and when other than DINP how much the phthalate ester of the determination target substance included in the product is identical with DINP, etc.

As described above, in order to evaluate the adequacy of the present analysis method, DEHP is included in the product A, and DINP is included in the product B. In the above example, it is determined that the phthalate ester included in the product A is other than DINP (DEHP), when the determination target table 600A that is obtained for the product A is used. Also, it is determined that the phthalate ester included in the product B is DINP, when the determination target table 600B that is obtained for the product B is used. This indicates that the present analysis method can be utilized in determination of whether the phthalate ester included in a product, such as cable covering material, is identical with the known phthalate esters, and determination of the type of the phthalate ester included in the product.

The present analysis method can accurately analyze which phthalate ester is included in the product in a simple and convenient manner, as compared with the gas chromatography mass spectrometry and the liquid chromatography mass spectrometry. In this regard, the present analysis method can be preferably used at a production plant that inspect products including phthalate ester to determine whether the products are acceptable, for example.

Note that, in the above example, the DINP signs in the determination criterion table 500 are generated by comparing the peak levels of DINP with the intermediate values, and are compared with the signs of the determination target table 600A or 600B. Alternatively, the DEHP signs in the determination criterion table 500 may be generated by comparing the peak levels of DEHP with the intermediate values, and are compared with the signs of the determination target table 600A or 600B. This process can evaluate whether the phthalate ester of the determination target substance included in the product is DEHP or other than DEHP, and when other than DEHP, to what degree the phthalate ester of the determination target substance included in the product is identical with DEHP, etc.

The present analysis method is also applicable to a combination of other phthalate esters in the same way as the combination of DEHP and DINP as in the above example.

The processing function of the above analysis apparatus 400 can be implemented by using a computer.

Figure 21:
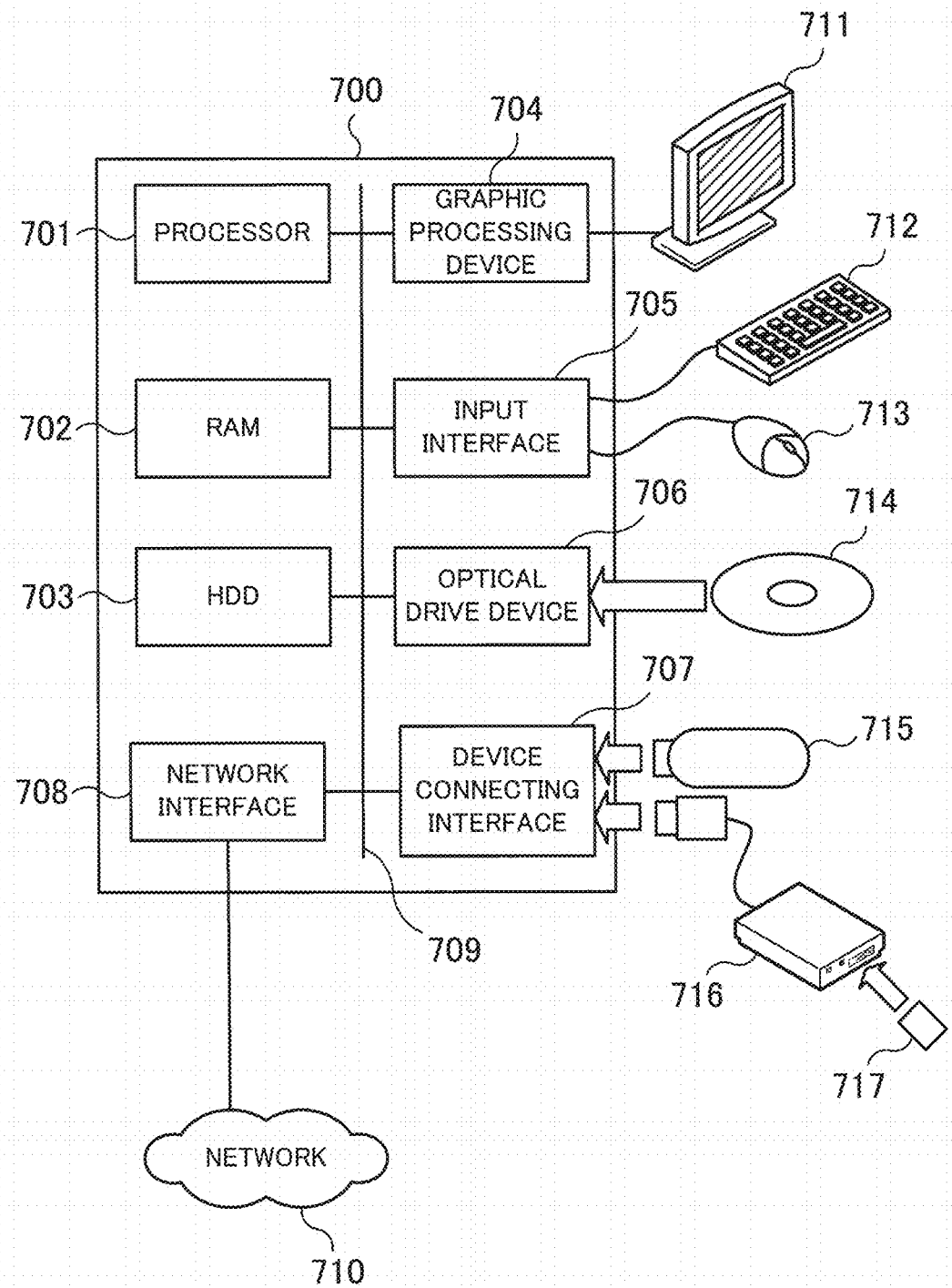
FIG. 21 illustrates an example of a hardware configuration of a computer.

FIG. 21 illustrates an example of a hardware configuration of a computer.

An entirety of a computer 700 is controlled by a processor 701. A random access memory (RAM) 702 and a plurality of peripheral devices are connected to the processor 701 via a bus 709. The processor 701 may be a multiprocessor. The processor 701 is a central processing unit (CPU), a micro processing unit (MPU), a digital signal processor (DSP), an application specific integrated circuit (ASIC), or a programmable logic device (PLD), for example. Also, the processor 701 may be a combination of two or more elements of the CPU, the MPU, the DSP, the ASIC, and the PLD.

The RAM 702 is used as a main memory device of the computer 700. In the RAM 702, at least a part of operating system (OS) programs and application programs executed by the processor 701 is temporarily stored. Also, various types of data used in processing by the processor 701 is stored in the RAM 702.

The peripheral devices connected to the bus 709 are a hard disk drive (HDD) 703, a graphic processing device 704, an input interface 705, an optical drive device 706, a device connecting interface 707, and a network interface 708.

The HDD 703 writes data into, and reads data from, an internal disk magnetically. The HDD 703 is used as an auxiliary memory device of the computer 700. In the HDD 703, OS programs, application programs, and various types of data are stored. Note that a semiconductor memory device, such as a flash memory, can also be used as the auxiliary memory device.

A monitor 711 is connected to the graphic processing device 704. The graphic processing device 704 displays an image on a screen of the monitor 711 in accordance with a command from the processor 701. The monitor 711 is a display device using a cathode ray tube (CRT), a liquid crystal display device, or the like.

A keyboard 712 and a mouse 713 are connected to the input interface 705. The input interface 705 transmits a signal sent from the keyboard 712 and the mouse 713 to the processor 701. Note that the mouse 713 is an example of a pointing device, and another pointing device can be used. Another pointing device is a touch panel, a tablet, a touch pad, a trackball, or the like.

The optical drive device 706 reads data recorded in an optical disc 714 by utilizing laser light or the like. The optical disc 714 is a portable storage medium in which data is recorded in a readable manner by reflection of light. The optical disc 714 is a digital versatile disc (DVD), a DVD-RAM, a compact disc read only memory (CD-ROM), a CD-R (Recordable)/RW (ReWritable), or the like.

The device connecting interface 707 is a communication interface for connecting peripheral devices to the computer 700. For example, a memory device 715 and a memory reader/writer 716 can be connected to the device connecting interface 707. The memory device 715 is a storage medium provided with a communication function with the device connecting interface 707. The memory reader/writer 716 writes data into a memory card 717 or reads data from the memory card 717. The memory card 717 is a storage medium having a shape of a card.

The network interface 708 is connected to a network 710. The network interface 708 transmits data to, and receives data from, another computer or communication device via the network 710.

The processing function of the analysis apparatus 400 can be implemented by the above hardware configuration.

The computer 700 provides the processing function of the analysis apparatus 400, by executing a program that is recorded in a computer-readable storage medium, for example. The program describing the procedure executed by the computer 700 may be stored in various storage media. For example, the program executed by the computer 700 can be stored in the HDD 703. The processor 701 loads at least a part of the program from the HDD 703 to the RAM 702, in order to execute the program. Also, the program executed by the computer 700 may be recorded in a portable storage medium, such as the optical disc 714, the memory device 715, and the memory card 717. The program stored in the portable storage medium becomes executable after installed in the HDD 703 by the control from the processor 701, for example. Also, the processor 701 may read out and execute the program directly from the portable storage medium.

Note that, in the above description, a metal reflection IR spectrum is obtained by using the infrared spectroscopy. Moreover, the above method of causing the different phthalate esters to adhere to predetermined base films can be applied to a Raman spectrum obtained by using a Raman spectroscopy in order to obtain a Raman spectrum including a distinguishable significant difference. Also, a phthalate ester included in a product or the like can be determined by using such a Raman spectrum. Also, the present disclosure can be applied to any measurement means which is unable to be distinguished when not adhering to a base film but generates a difference in spectrum when adhering to a base film.

According to the disclosed technology, significantly different spectra can be acquired from different phthalate esters. Also, such spectra can be used to accurately identify the types of the phthalate esters.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. An analysis method comprising:
preparing a first specimen and a second specimen, the first specimen being that a first phthalate ester adheres to a first base film, the second specimen being that a second phthalate ester adheres to a second base film of a same type as the first base film, the first phthalate ester adhering to the first base film and the second phthalate ester adhering to the second base film being in different states; and
acquiring a first spectrum and a second spectrum by radiating electromagnetic waves on the first specimen and the second specimen, respectively.

2. The analysis method according to claim 1, wherein the different states of the first phthalate ester and the second phthalate ester result from adherence states of the first phthalate ester and the second phthalate ester that adhere to the first base film and the second base film in different states from the first phthalate ester and the second phthalate ester existing solitarily, and different absorption states of the first phthalate ester and the second phthalate ester that are absorbed into the first base film and the second base film.

3. The analysis method according to claim 2, wherein the preparing includes preparing the first specimen in which the first phthalate ester is absorbed in the first base film, and the second specimen in which the second phthalate ester remains on a surface of the second base film.

4. The analysis method according to claim 1, further comprising:
preparing a third specimen in which a determination target substance, for which identicalness with the first phthalate ester or the second phthalate ester is to be determined, adheres to a third base film of a same type as the first base film and the second base film;
acquiring a third spectrum by radiating an electromagnetic wave on the third specimen; and
determining whether the determination target substance is identical with the first phthalate ester or the second phthalate ester, by using the first spectrum, the second spectrum, and the third spectrum.

5. The analysis method according to claim 4, wherein the determining includes:
normalizing the first spectrum, the second spectrum, and the third spectrum, by using base lines, and levels at a common reference peak position, of the first spectrum, the second spectrum, and the third spectrum;
generating a first intermediate value between different levels at a first peak position of the normalized first spectrum and the normalized second spectrum;
determining whether a level at the first peak position of the normalized third spectrum is larger or smaller than the first intermediate value; and
determining the identicalness of the determination target substance, based on whether the level at the first peak position of the normalized third spectrum is larger or smaller than the first intermediate value.

6. The analysis method according to claim 5, wherein the determining the identicalness further includes:
generating a second intermediate value between different levels at a second peak position of the normalized first spectrum and the normalized second spectrum;
determining whether a level at the second peak position of the normalized third spectrum is larger or smaller than the second intermediate value; and
determining the identicalness of the determination target substance, based on whether the level at the first peak position of the normalized third spectrum is larger or smaller than the first intermediate value and whether the level at the second peak position of the normalized third spectrum is larger or smaller than the second intermediate value.

7. The analysis method according to claim 4, wherein the acquiring the first spectrum, the second spectrum, and the third spectrum includes acquiring a group of difference spectra between a group of spectra that are measured by radiating electromagnetic waves on the first specimen, the second specimen, and the third specimen and a blank spectrum measured by radiating an electromagnetic wave on the first base film or the second base film, as the first spectrum, the second spectrum, and the third spectrum.

8. The analysis method according to claim 4, wherein the preparing the third specimen includes causing steam of the determination target substance generated by heating a fourth specimen including the determination target substance to adhere to the third base film.

9. An analysis apparatus comprising:
a first acquisition unit configured to acquire and measure a first spectrum and a second spectrum by radiating electromagnetic waves on a first specimen and a second specimen respectively, the first specimen being that a first phthalate ester adheres to a first base film, the second specimen being that a second phthalate ester adheres to a second base film of a same type as the first base film, the first phthalate ester adhering to the first base film and the second phthalate ester adhering to the second base film being in different states;
a second acquisition unit configured to acquire and measure a third spectrum by radiating an electromagnetic wave on a third specimen in which a determination target substance, for which identicalness with the first phthalate ester or the second phthalate ester is to be determined, adheres to a third base film of a same type as the first base film and the second base film; and a first determination unit configured to determine whether the determination target substance is identical with the first phthalate ester or the second phthalate ester, by using the first spectrum and the second spectrum acquired by the first acquisition unit and the third spectrum acquired by the second acquisition unit.

10. The analysis apparatus according to claim 9, wherein the first determination unit includes:
a normalization unit configured to normalize the first spectrum and the second spectrum acquired by the first acquisition unit and the third spectrum acquired by the second acquisition unit, by using base lines, and levels at a common reference peak position, of the first spectrum, the second spectrum, and third spectrum;
a generation unit configured to generate a first intermediate value between different levels at a first peak position of the first spectrum and the second spectrum normalized by the normalization unit;
a second determination unit configured to determine whether a level at the first peak position of the third spectrum normalized by the normalization unit is larger or smaller than the first intermediate value; and
a third determination unit configured to determine the identicalness of the determination target substance, based on a determination result by the second determination unit.

11. The analysis apparatus according to claim 9, wherein the first acquisition unit and the second acquisition unit acquire a group of difference spectra between a group of spectra measured by radiating electromagnetic waves on the first specimen, the second specimen, and the third specimen and a blank spectrum measured by radiating an electromagnetic wave on the first base film or the second base film, as the first spectrum, the second spectrum, and the third spectrum.

12. A non-transitory computer-readable storage medium storing an analysis program that causes a computer to perform a procedure comprising:
acquiring and measuring a first spectrum and a second spectrum by radiating electromagnetic waves on a first specimen and a second specimen, respectively, the first specimen being that a first phthalate ester adheres to a first base film, the second specimen being that a second phthalate ester adheres to a second base film of a same type as the first base film, the first phthalate ester adhering to the first base film and the second phthalate ester adhering to the second base film being in different states;
acquiring and measuring a third spectrum by radiating an electromagnetic wave on a third specimen in which a determination target substance, for which identicalness with the first phthalate ester or the second phthalate ester is to be determined, adheres to a third base film of a same type as the first base film and the second base film; and
determining whether the determination target substance is identical with the first phthalate ester or the second phthalate ester, by using the first spectrum, the second spectrum, and the third spectrum.

13. The non-transitory computer-readable storage medium according to claim 12, wherein
the determining includes:
normalizing the first spectrum, the second spectrum, and the third spectrum, by using base lines, and levels at a common reference peak position, of the first spectrum, the second spectrum, and the third spectrum;
generating a first intermediate value between different levels at a first peak position of the normalized first spectrum and the normalized second spectrum;
determining whether a level at the first peak position of the normalized third spectrum is larger or smaller than the first intermediate value; and
determining the identicalness of the determination target substance, based on whether the level at the first peak position of the normalized third spectrum is larger or smaller than the first intermediate value.

14. The non-transitory computer-readable storage medium according to claim 12, wherein
in acquiring the first spectrum, the second spectrum, and the third spectrum, a group of difference spectra between a group of spectra measured by radiating electromagnetic waves on the first specimen, the second specimen, and the third specimen and a blank spectrum measured by radiating an electromagnetic wave on the first base film or the second base film is acquired as the first spectrum, the second spectrum, and the third spectrum.

* * * * *